United States Patent
Naito et al.

(10) Patent No.: US 6,569,087 B2
(45) Date of Patent: May 27, 2003

(54) ENDOSCOPE

(75) Inventors: Kan Naito, Hachioji (JP); Atsushi Watanabe, Hino (JP); Hideo Ito, Akishima (JP); Takayasu Miyagi, Hachioji (JP); Michio Sato, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 128 days.

(21) Appl. No.: 09/811,721

(22) Filed: Mar. 19, 2001

(65) Prior Publication Data
US 2001/0025135 A1 Sep. 27, 2001

(30) Foreign Application Priority Data
Mar. 21, 2000 (JP) ........................................ 2000-078728

(51) Int. Cl.[7] .................................................. A61B 1/12
(52) U.S. Cl. ........................................ 600/156; 600/132
(58) Field of Search ................................ 600/156, 131, 600/132, 133, 158, 159, 153, 155, 157, 151, 154

(56) References Cited

U.S. PATENT DOCUMENTS 5,575,752 A * 11/1996 Yabe et al. ............... 600/121
5,888,191 A 3/1999 Akiba et al.

FOREIGN PATENT DOCUMENTS

| JP | 3-99627 | 4/1991 |
|---|---|---|
| JP | 4-307022 | 10/1992 |
| JP | 5-317240 | 12/1993 |

* cited by examiner

*Primary Examiner*—Teresa Walberg
*Assistant Examiner*—Thor Campbell

(57) ABSTRACT

An endoscope capable of improving assembly operativity and facilitating a repair operation is provided. This endoscope has an insertion section having a proximal end portion and a distal end portion, and inserted into a body cavity, an operation section arranged on a proximal end portion side of the insertion section, a universal cord extending from the operation section, and having a distal end portion, and a conduit extended in the insertion section, the operation section and the universal cord. This conduit has one end arranged on the distal end portion of the insertion section and having a first opening portion formed therein and the other end arranged on the connector and having a second opening portion formed therein, and separable on a portion between one end and the other end.

35 Claims, 25 Drawing Sheets

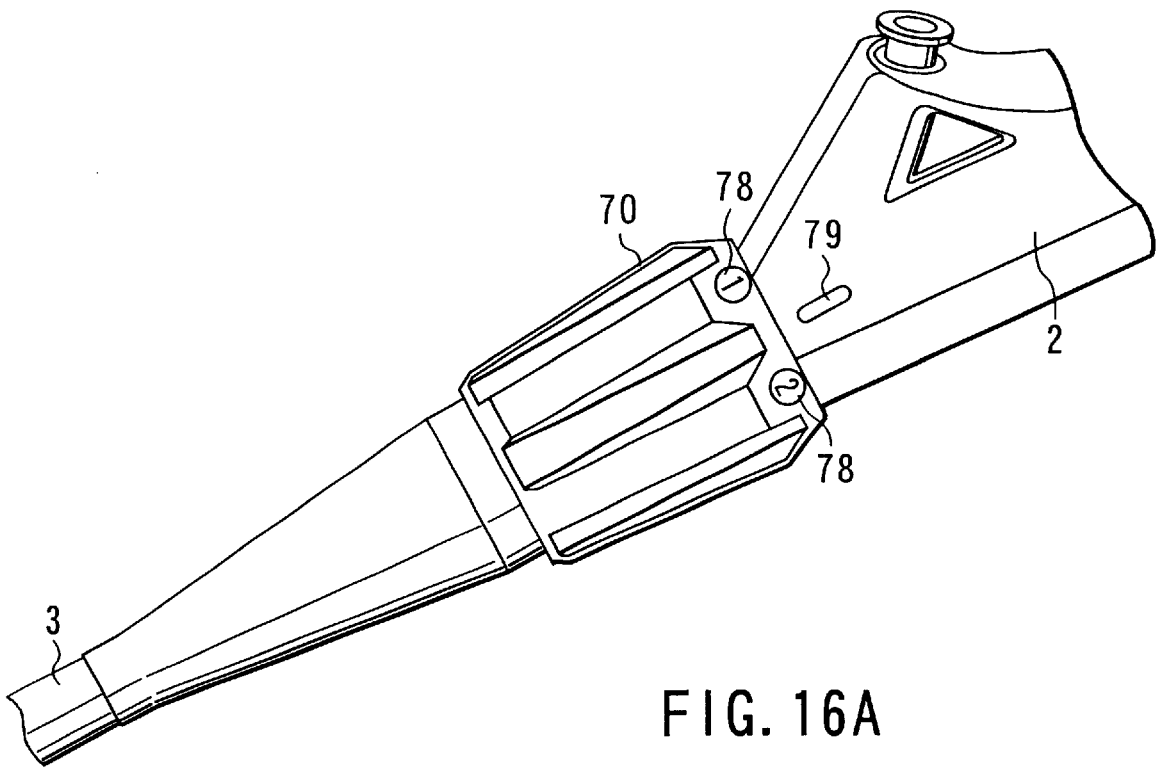
FIG. 16A
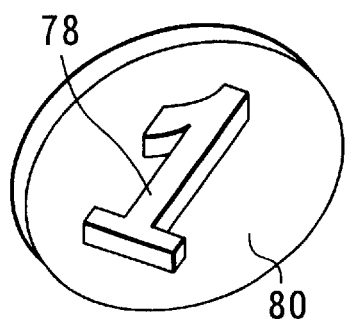 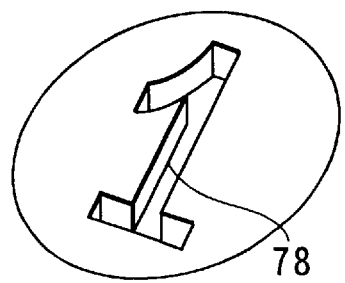
FIG. 16B          FIG. 16C

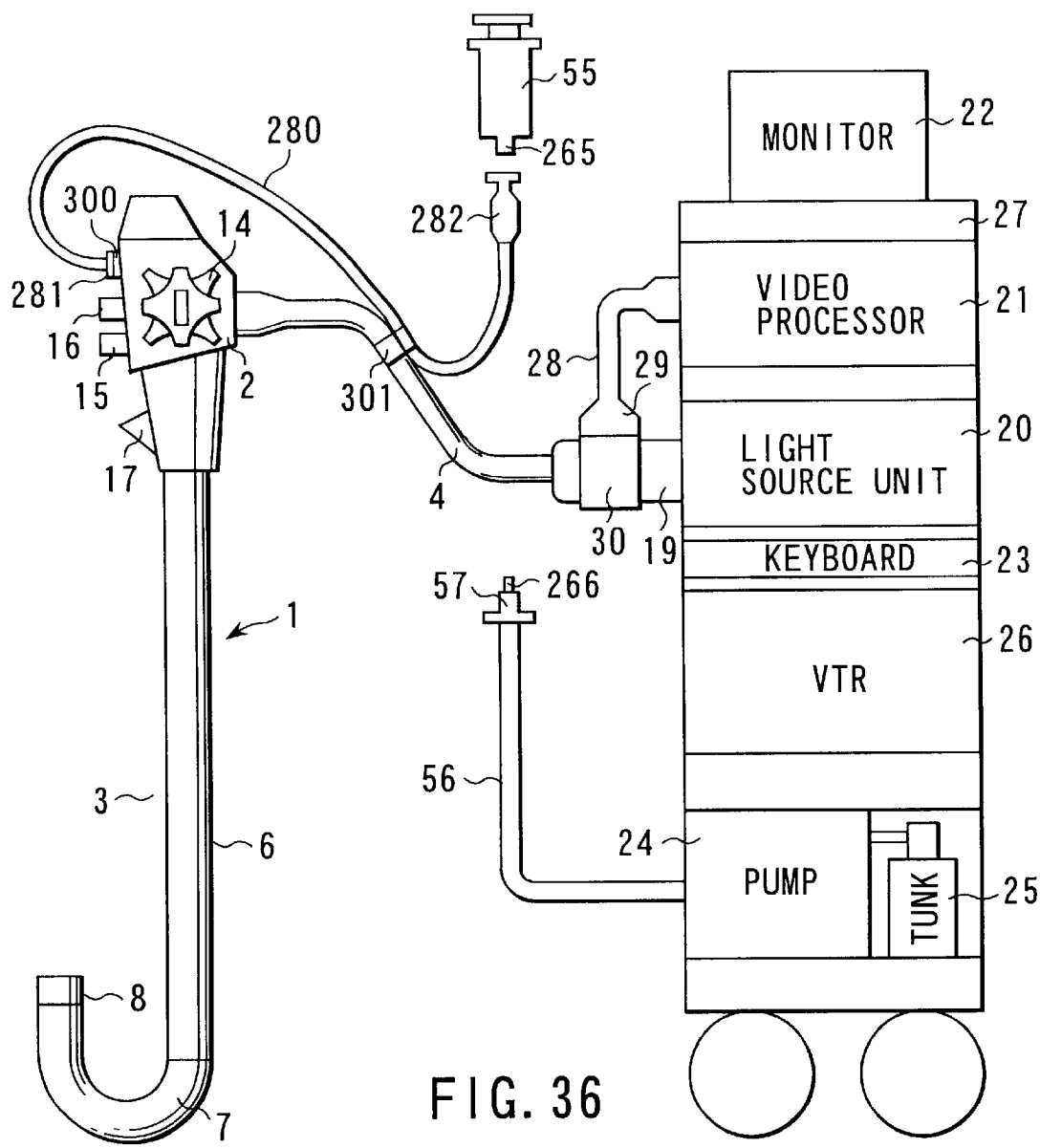
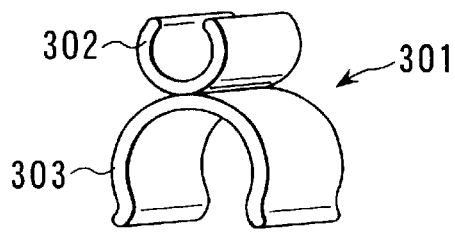
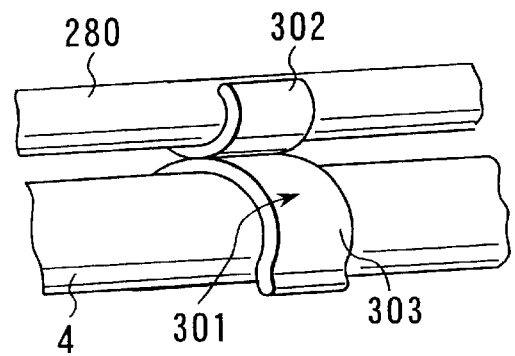
FIG. 36
FIG. 37
FIG. 38

ENDOSCOPE

CROSS-REFERENCE TO RELATED APPLICATIONS

This application is based upon and claims the benefit of priority from the prior Japanese Patent Application No. 2000-078728, filed Mar. 21, 2000, the entire contents of which are incorporated herein by reference.

BACKGROUND OF THE INVENTION

The present invention relates to an endoscope having an air/water supply conduit provided therein.

Jpn. Pat. Appln. KOKAI Publication No. 4-307022, for example, discloses an endoscope having an air/water supply function. This endoscope has a water supply nozzle directed toward an observation window and provided on the distal end of an insertion section inserted into a body cavity. When the surface of the observation window is stained, water is sprayed from the water supply nozzle onto the surface of the observation window by the pressure of a pump included in a light source unit to wash away the stain on the surface of the observation window.

In addition, Jpn. Pat. Appln. KOKAI Publication No. 3-99627 discloses an endoscope having a suction function and a forward water supply function. This endoscope can attract the dirt, mucus and the like which obstruct observation and discharge them out of a body cavity. Further, as in the case of the interior of, for example, large intestine, if a dirt or the like is attached to an observation target, cleaning water is strongly sprayed from a forward water supply port opening in forward direction onto the distal end of the insertion section to thereby wash away the dirt or the like strongly adhering to the target. Water supply in this case is carried out by connecting a manually-operated water supply equipment such as a syringe to the inlet of a water supply conduit leading to the forward water supply port.

Further, Jpn. Pat. Appln. KOKAI Publication No. 5-317240 discloses an endoscope having a stopper valve provided on a water supply conduit. When this endoscope is pulled out from a body cavity, water remaining in the forward water supply conduit of the endoscope can be prevented from leaking outside from the inlet of the conduit.

Such an endoscope having the air/water supply function, the suction function and the forward water supply function comprises a conduit extending from the distal end portion of the insertion section to the distal end portion of a universal cord through an operation section. The conduit is formed out of one tube of, for example, PTFE. This tube normally has a length of 2000 mm to 5000 mm, which length varies according to the type of the endoscope. When assembling the endoscope, the tube is connected to the distal end portion of the insertion section, gradually inserted from the distal end portion side of the insertion section into the insertion section and inserted into the universal cord through the operation section. During an assembly line for assembling the endoscope, the long tube is exposed as described above. Due to this, there is a probability that the tube is entangled with other members to disadvantageously hinder the assembly operation or the tube interferes with the other members to damage the tube.

Furthermore, if the tube is damaged while the endoscope is used or cleaned, it is necessary to replace the tube with a new one. In that case, since the conduit is formed out of one tube, it is required to disassemble the endoscope entirely to replace the tube with a new one, disadvantageously requiring lot of labor for the repair operation.

BRIEF SUMMARY OF THE INVENTION

The present invention has been made in view of the above-stated circumstances. It is, therefore, an object of the present invention to provide an endoscope capable of improving the assembly operativity of the endoscope and facilitating a repair operation.

According to one aspect of the invention to obtain the above object, there is provided an endoscope comprising: an insertion section having a proximal end portion and a distal end portion, and being insertable into a body cavity; an operation section arranged on a proximal end portion side of the insertion section; a universal cord extending from the operation section, and having a distal end portion; and a conduit inserted into the insertion section, the operation section and the universal cord, wherein the conduit has one end arranged on the distal end portion of the insertion section and having a first opening portion formed therein, and the other end arranged on the universal cord and having a second opening portion formed therein, the conduit separable on a portion between the one end and the other end.

According to this endoscope, the conduit communicating the distal end portion of the insertion section through the operation section to the distal end portion of the universal cord is divided into pieces which are connected to each other in a detachable manner, thereby the assembly operativity of the endoscope can be improved and the endoscope can be repaired easily.

It is preferable that the conduit has a dividable portion arranged in the operation section. Further, it is preferable that the conduit includes a conduit selected from a group consisting of a forward water supply conduit, an air/water supply conduit, a suction conduit and an air supply conduit. In this case, the conduit is included in the insertion section and in the universal cord, respectively and then the conduit is connected within, for example, the operation section, whereby the forward water supply conduit, the air/water supply conduit, the suction conduit, the air supply conduit or the like can be constituted. Further, if the conduit is damaged, only the damaged conduit can be replaced with a new one.

According to another aspect of the present invention, there is provided an endoscope comprising: an insertion section having a proximal end portion and distal end portion, and being insertable into a body cavity; an operation section arranged on a distal end portion side of the insertion section; a universal cord extending from the insertion section, and having a distal end portion; a connector provided on the distal end portion of the universal cord; and a conduit inserted into the insertion section, the operation section and the universal cord, wherein the conduit has one end arranged on the distal end portion of the insertion section and having a first opening portion formed therein, and the other end arranged on the connector and having a second opening portion formed therein, the conduit separable on a portion between the one end and the other end.

According to yet another aspect of the present invention, there is provided an endoscope system comprising: an insertion section having a proximal end portion and a distal end portion, and being insertable into a body cavity; an operation section arranged on a proximal end portion side of the insertion section; a universal cord extending from the operation section, and having a distal end portion; a connector provided on the distal end portion of the universal cord; a conduit inserted into the insertion section, the operation section and the universal cord, and having one end arranged on the distal end portion of the insertion section and having a first opening portion formed therein and the other end arranged on the connector and having a second opening portion formed therein; a fluid supply source supplying a fluid to the conduit; and a valve having a first connection section attachable and detachable to the second opening portion and a second connection section attachable and detachable to the fluid supply source, and preventing backflow of the fluid when feeding the fluid supplied from the fluid supply source to the conduit.

According to this endoscope system, there is no need to provide a valve for preventing the backflow of a fluid in the endoscope itself. Therefore, the endoscope itself can be made light in weight, small in size and simple in structure, the operativity of the endoscope is thereby improved and the endoscope can be carried more easily. Besides, the production cost of the endoscope and the like can be reduced. In addition, since no complex check-valve is provided on the endoscope side, a defect does not occur to parts relating to the check-valve and a repair operation for the fault of the endoscope resulting from the defect is not required.

Moreover, it is preferable that a supply tube including the valve is provided and that the first connection section and the second connection section are formed in the supply tube. In this case, a water supply tube having a valve is formed and the fluid supply source can be attached and detached to and from the endoscope without laying a load on the endoscope. In addition, since the fluid supply source is connected to the endoscope using the value equipped water supply tube, it is possible to carry out attachment/detachment operations for the supply source in a place away from the endoscope, thereby making the attachment/detachment operations easier and simpler. Normally, there is not enough space in the connection section of the endoscope for connecting the value equipped water supply tube. Even so, it is possible to provide a structure capable of connecting the value equipped water supply tube in a compact fashion. Besides, the flexibility for the layout of the endoscope system is increased.

Furthermore, it is preferable that a portion between the first connection section and the second opening portion is formed to have a structure requiring more time in attachment and detachment operations for attaching and detaching the first connection section to and from the opening portion than attachment and detachment operations for attaching and detaching the second connection section to and from the fluid supply source. In this case, an operator attaches and detaches the fluid supply source to and from the value equipped water supply tube without detaching the valve or value equipped water supply tube for preventing the backflow of a fluid from the endoscope, thereby making it possible to prevent the valve or the value equipped water supply tube from being erroneously detached.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 16A is a perspective view showing a modification of the operation section of an endoscope, and FIGS. 16B and 16C are enlarged, perspective views showing numbers given to a knob;

FIG. 36 is an explanatory view for schematically showing the overall constitution of an endoscope system according to the eleventh embodiment of the present invention;

FIG. 37 is a perspective view of the binding clip of the endoscope system shown in FIG. 36; and FIG. 38 is a perspective view showing a state in which the binding clip shown in FIG. 36 is used.

DETAILED DESCRIPTION OF THE INVENTION

The embodiments of the present invention will be described hereinafter with reference to the drawings.

Figure 1:
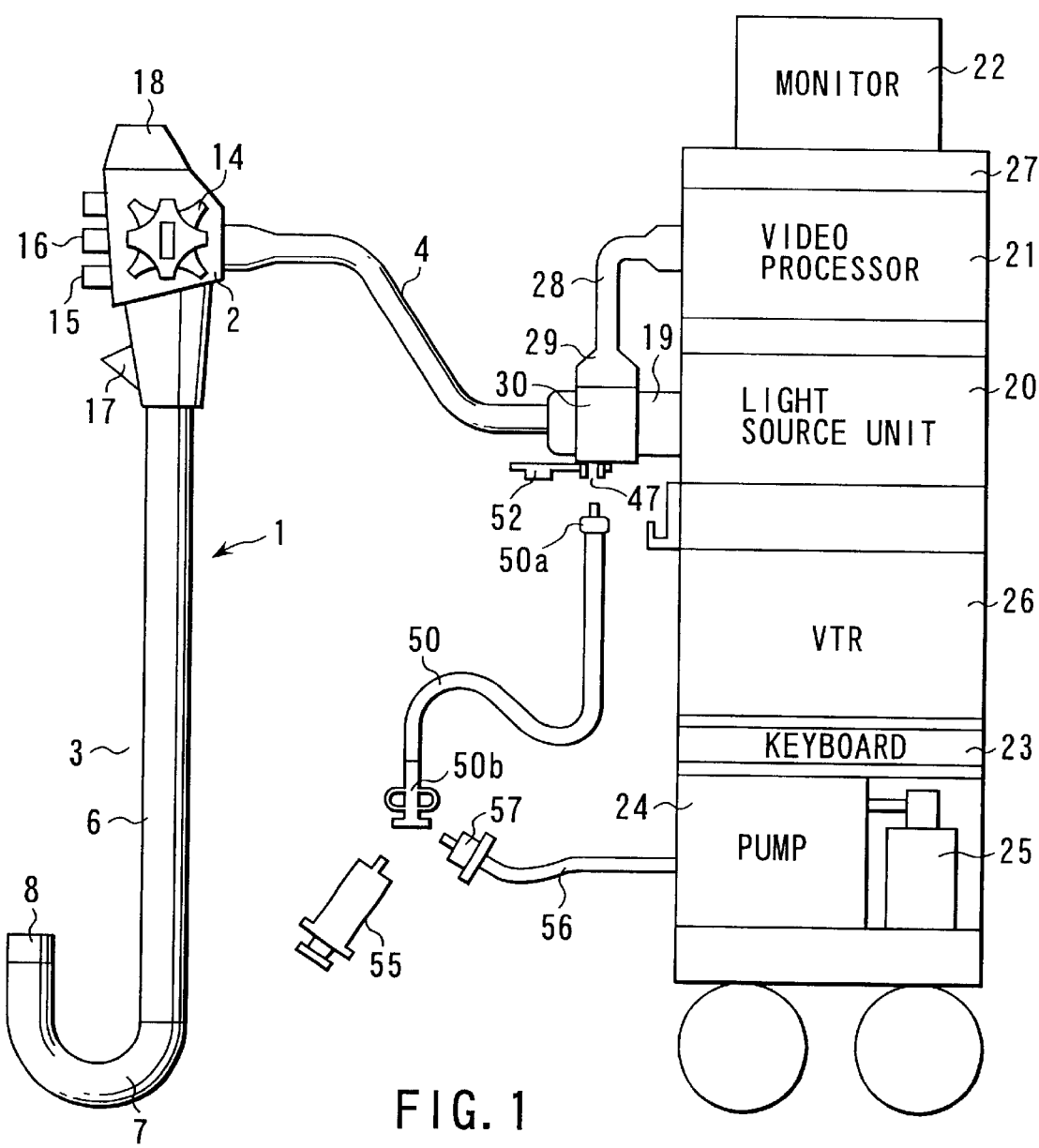
FIG. 1 is an explanatory view for schematically showing the overall constitution of an endoscope system according to the first embodiment of the present invention.

FIGS. 1 to 8 show the first preferred embodiment of the present invention. FIG. 1 is an overall view of an endoscope system according to the first embodiment. As shown in FIG. 1, an endoscope 1 comprises an operation section 2, an insertion section 3 and a universal cord (or light guide cable) 4. The insertion section 3 is constituted by coupling a flexible tube 6, a bending tube and a distal end portion 8 in an order starting with the operation section 2 side. In the insertion section 3, a treatment tool insertion channel conduit, an air/water supply channel conduit and a forward water supply channel conduit, which are not shown in FIG. 1, are provided and the internal elements of an endoscope are arranged.

Figure 2:
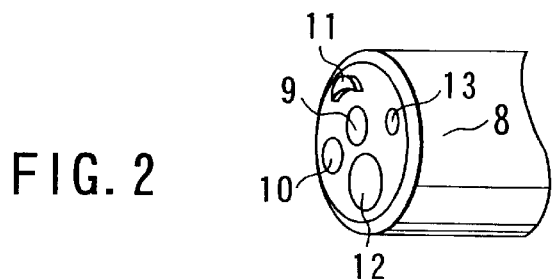
FIG. 2 is a perspective view of the distal end portion of an endoscope according to the first embodiment.

As show in FIG. 2, an observation window 9, an illumination window 10, an air/water supply nozzle 11 leading to the air/water supply conduit, a distal end opening 12 leading to the treatment tool insertion channel and a forward water supply port 13 serving as an opening portion leading to the forward water supply conduit to be described later and opening in forward direction, are formed on the distal end portion 8.

As shown in FIG. 1, a bending operation knob section 14 for bending the bending tube 7 of the insertion section 3 in vertical and horizontal directions, an air/water supply button 15 for selectively spraying a fluid such as water or air onto the outer surface of the observation window 9 from the air/water supply nozzle 11 through the air/water supply conduit and for cleaning the outer surface, a suction operation button 16 for sucking and drawing mucus and the like in a body cavity through the treatment tool insertion channel, an insertion port 17 leading to the treatment tool insertion channel and a switch operation section 18 are provided on the operation section 2.

A connector 19 serving as an opening portion is provided on the extended distal end portion of the universal cord 4. The connector 19 is connected to a light source unit 20 which is one of external devices. The external devices involve an image processor 21, a monitor 22, an input keyboard 23, a water supply pump 24 consisting of a roller pump, a water tank 25 (or a pigment tank), a VTR 26, a suction pump unit which is not shown in FIG. 1 and the like as well as the light source unit. These equipment are disposed on a carrier equipped rack (or trolley) 27.

The connector 19 is provided with many functions including a light guide tube connected to the light source unit 20, an electrical contact section, a connection section 30 connecting the electrical connector 29 of a cord 28 connected to the image processor (or video processor) 21 as well as an air supply mouthpiece and a water supply mouthpiece which are not shown in FIG. 1.

Figures 3, 4A, 4B:
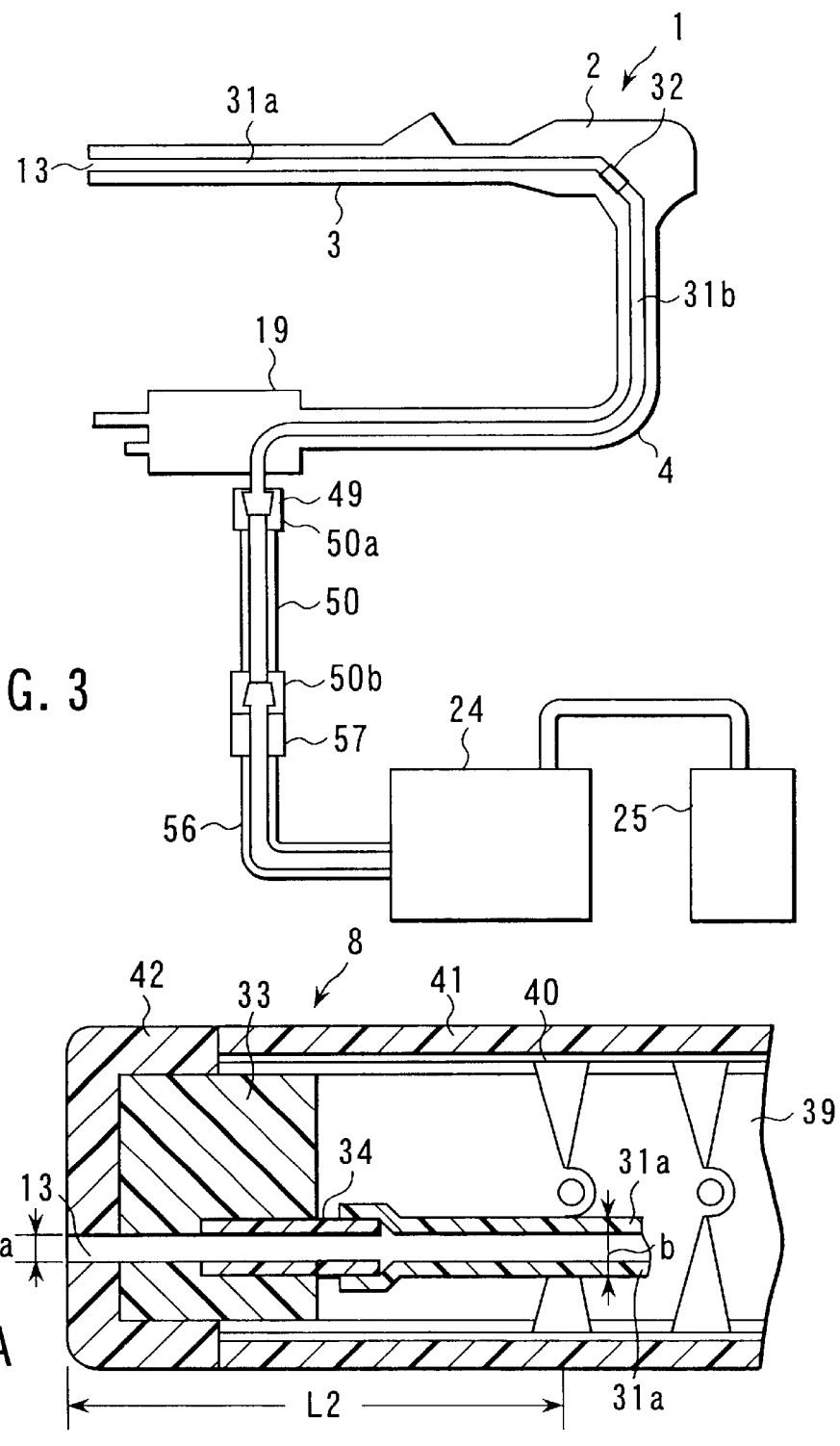
FIG. 3 is a schematic block diagram showing the forward water supply conduit of the endoscope system according to the first embodiment.
FIGS. 4A and 4B are a longitudinal section view of the distal end portion of the endoscope and a side view of a cleaning brush according to the first embodiment.

As shown in FIG. 3, water supply tubes 31a and 31b forming the forward water supply conduit are extended in the insertion section 3, the operation section 2 and the universal cord 4 of the endoscope 1. Each of the water supply tubes 31a and 31b is formed out of a flexible tube made of fluoroplastic such as PTFE and having an inside diameter ø of about 1.5 mm. These water supply tubes 31a and 31b are connected to each other by a connection member 32, which will be described later, arranged within the operation section 2 to provide an overall length of about 4000 mm.

The distal end portion of the water supply tube 31a included in the insertion section 3 is connected to a forward water supply port 13 as shown in FIG. 4A. Namely, the distal end portion 8 has a rigid portion 33 on which the forward water supply port 13 is formed, the distal end portion of the pipe 34 is concentrically connected to the forward water supply port 13, and the distal end portion of the water supply tube 31a is connected to the rear end portion of the pipe 34.

If it is assumed that the inside diameter ø of the pipe 34 is "a" and the inside diameter ø of the water supply tube 31a is "b", the relationship of a and b is a<b. Therefore, the water supplied through the water supply tube 31a is accelerated by the pipe 34 and then fed from the forward water supply port 13. A reference 35 shown in FIG. 4B denotes a cleaning brush for cleaning the interior of the forward water supply port 13 and the interior of the pipe 34. This cleaning brush 35 is provided with a brush rod 37 having a handle 36 and brush bristles 38 are provided on the distal end portion of the brush rod. The length L1 of the brush rod 37 is set slightly shorter than the length L2 of the rigid portion 33 of the distal end portion 8. The cleaning brush 35 is inserted from the distal end of the forward water supply port 13 to clean the interior of the forward water supply port 13 and that of the pipe 34.

The bending tube 7 has a plurality of pieces 39 pivotally attached to each other and can be bended in a required direction through the pivotal movements of these pieces. The outer peripheries of these curved pieces 39 are covered with a rubber layer 41 through a braid 40. Also, the outer periphery of the rigid portion 33 is covered with an insulating cover 42.

Figures 5, 6:
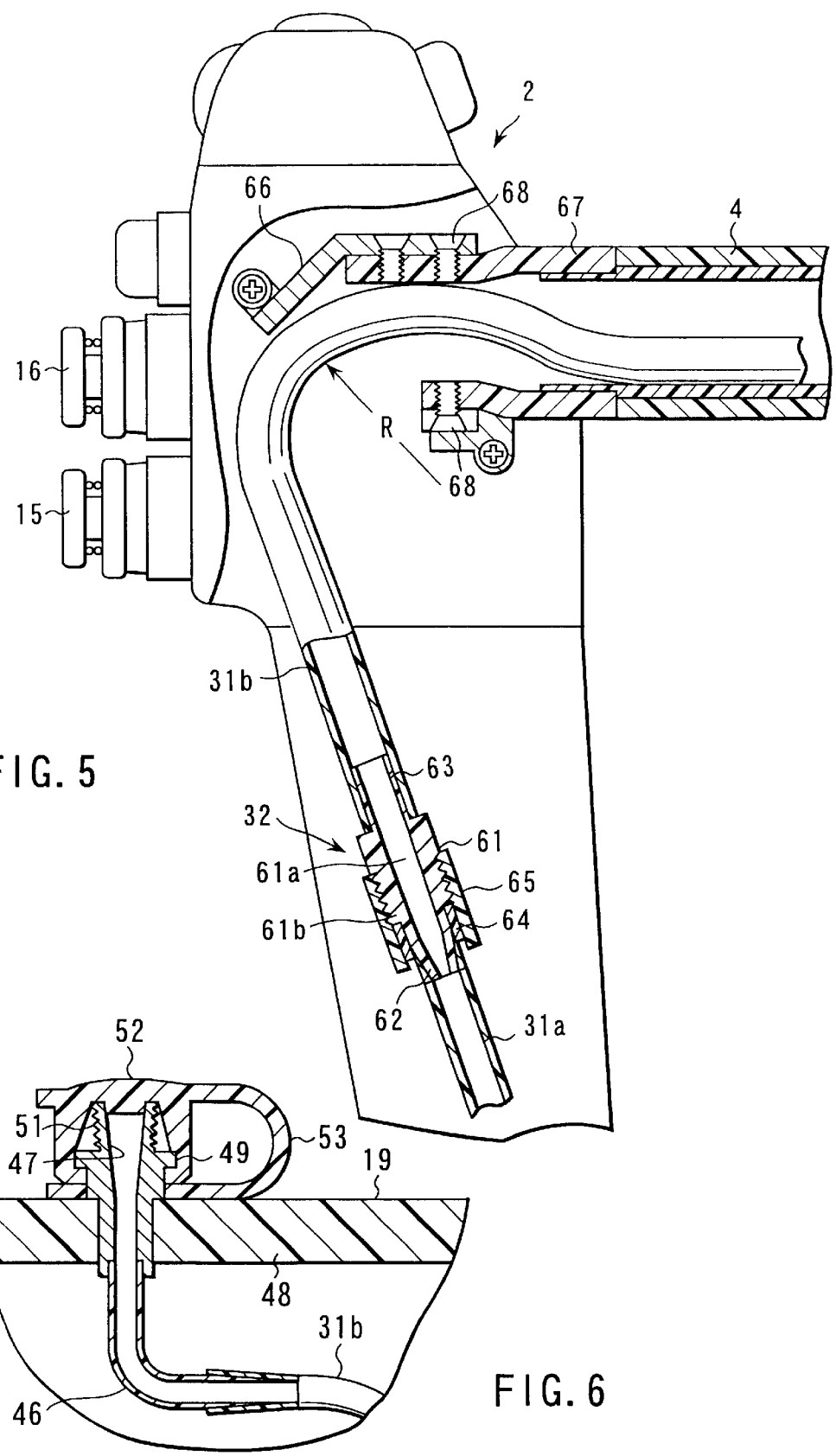
FIG. 5 is a side view showing a partly cut operation section of the endoscope according to the first embodiment.
FIG. 6 is a cross-sectional view showing a part of the connector of the endoscope according to the first embodiment.

The end portion of the water supply tube 31b included in the universal cord 4 extends toward the connector 19 as shown in FIG. 3. As shown in FIG. 6, the end portion of the water supply tube 31b is connected to a water supply port 47 through a hard pipe 46. This water supply port 47 has a mouthpiece 49 penetrating the exterior member 48 of the connector 19 and attached to the exterior member 48. The mouthpiece 49 is air and fluid-tightly attached to the exterior member 48. A male screw portion 51, with which the first connector 50a of an adapter tube 50 to be described later is screwed and to which the first connector 50a is connected, is provided on the outer periphery of the exposed distal end portion of the mouthpiece 49.

A cap 52 for closing the mouth portion of the mouthpiece 49 is provided. The cap 52 is connected to the mouthpiece 49 through a tongue piece 53. The cap 52 and the tongue piece 53 are formed integrally with each other by an elastic member. When the adapter tube 50 is not connected to the mouthpiece 49 of the endoscope 1, the cap 52 is put on the mouthpiece 49 to seal the mouth portion of the mouthpiece 49.

Further, as shown in FIG. 1, if a fluid is fed to the forward water supply conduit of the endoscope 1, a fluid supply source is connected to the mouthpiece 49 through the adapter tube 50. Here, as the fluid supply source, a manual water supply equipment, e.g., a syringe 55 or an automated water supply equipment or a water supply pump unit 24 can be connected to the mouthpiece 49. A flexible supply tube is connected to the water supply pump unit 24. A plug-in connector 57 is provided on the distal end of the supply tube 56. The plug-in connector 57 can be connected to the second connector 50b of the adapter tube 50.

Figure 7:
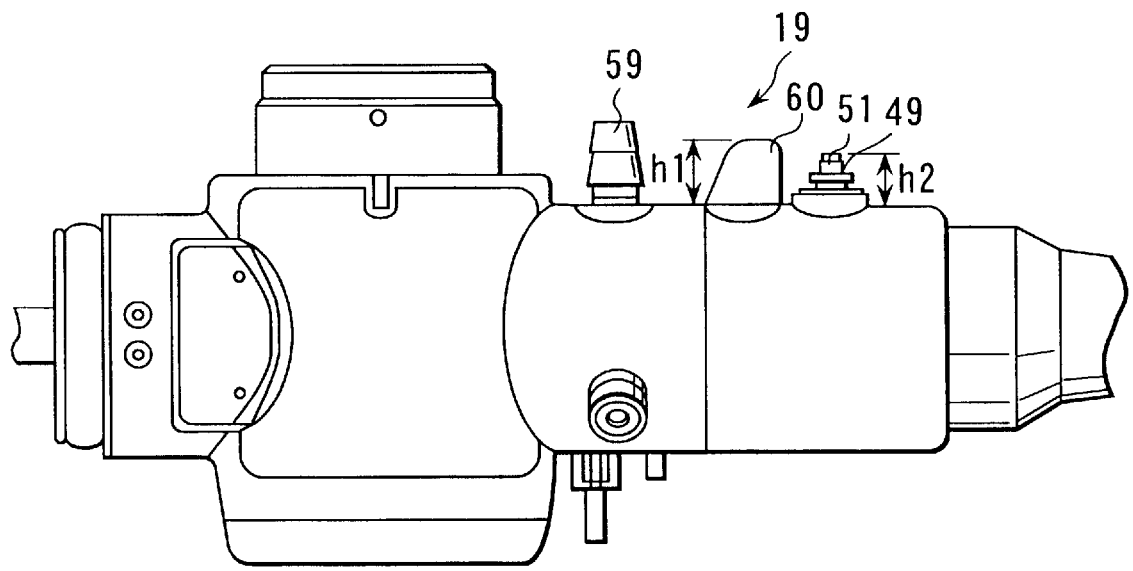
FIG. 7 is a side view of the connector of the endoscope according to the first embodiment.

Moreover, as shown in FIG. 7, the mouthpiece 49 provided on the outer wall of the connector 19 protrudes in the same direction as a suction mouthpiece 59, and the mouthpieces 49 and 59 are arranged almost in parallel. A guard section 60 comprising a protrusion is provided between the mouthpiece 49 and the suction mouthpiece 59. The height h1 of the guard section 60 and the height h2 of the mouthpiece 49 are set to have a relationship of h1>h2. Due to this, if a tube from a suction source, which is not shown, is attached to or detached from the suction mouthpiece 59, the guard section 60 protects the male screw portion 51 of the mouthpiece 49 from being touched with fingers.

Figure 8:
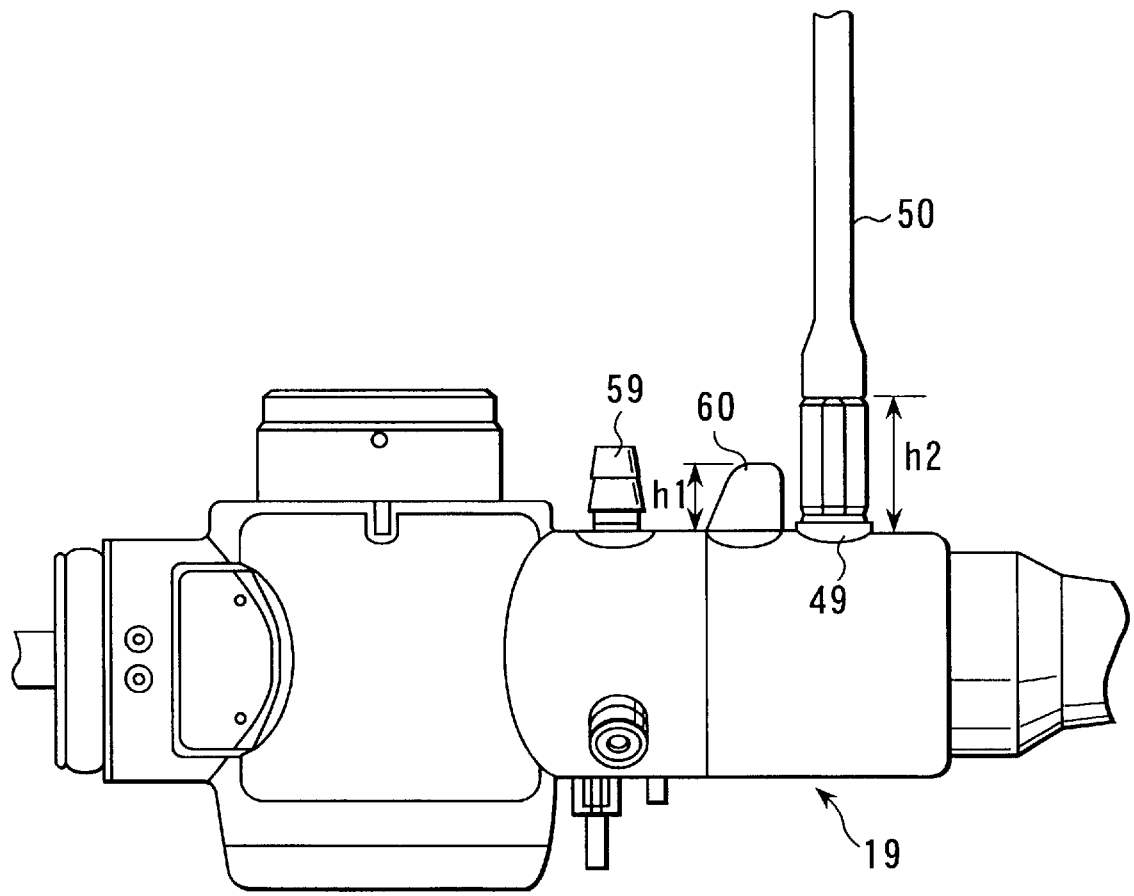
FIG. 8 is a side view of the connector of the endoscope according to the first embodiment.

In addition, as shown in FIG. 8, the first connector 50a of the adapter tube 50 has a height h3. The height h3 of the first connector 50a and the height h1 of the guard section 60 are set to have a relationship of h3>h1. Due to this, if the first connector 50a is attached to or detached from the mouthpiece 49, the guard section 60 does not hinder the attachment or detachment operation.

Next, the connection member 32 connecting the water supply tube 31a extended in the insertion section 3 to the water supply tube 31b extended in the universal cord 4 within the operation section 2 is constituted as shown in FIG. 5.

The connection member 32 in this embodiment has a connection mouthpiece 61 formed out of synthetic resin or the like. A water supply passage 61a is provided in the connection mouthpiece and a male screw portion 61b is provided on the outer peripheral portion of the connection mouthpiece 61. A taper section 62 is provided on one end portion of the connection mouthpiece 61 and a connection tube section 63 is provided on the other end portion of the connection mouthpiece 61. A taper tube 64 having a tapered inner peripheral surface corresponding to the taper section 62 is fitted into the taper section 62. The connection member 32 is also provided with a fastening nut 65 engaged with a taper tube 64 and screwed with the male screw portion 61b.

Accordingly, if the water supply tubes 31a and 31b are connected to each other by the connection member 32 constituted as stated above, the taper tube 64 and the fastening nut 65 are installed on the proximal end portion of one water supply tube 31a in advance. Then, the proximal end portion of the water supply tube 31a is fitted into the taper section 62 of the connection mouthpiece 61, the taper tube 64 is moved onto the taper section 62 and the fastening nut 65 fastens the male screw portion 61b. By doing so, the taper tube 64 is attracted toward the large outside diameter portion of the taper section 62 by the fastening nut 65 and the water supply tube 31a is fastened and fixed between the taper section 62 and the taper tube 64. Further, the proximal end portion of the other water supply tube 31b is fitted into the connection tube section 63 of the connection mouthpiece 61 and fixed thereto by an adhesive or the like in case of need, whereby the water supply tubes 31a and 31b can be connected to each other.

Therefore, while the water supply tube 31b is extended in the insertion section 3 and the water supply tube 31b is extended in the universal cord 4 during the assembly of the endoscope 1, these water supply tubes 31a and 31b can be connected to each other, in a detachable manner, through the connection member 32 within the operation section 2. Further, during the assembly of the endoscope 1, it is possible to prevent the long water supply tubes 31a and 31b from being pulled out from the endoscope 1 and entangled with each other and from interfering with other members, thereby making it possible to improve assembly operativity.

In addition, if the endoscope 1 is used for a long time and the water supply tube 31a is required to be replaced with a new tube because of damage, the casing of the operation section 2 is opened and the fastening nut 65 of the connection member 32 is loosened. By doing so, the water supply tube 31a of the connection member 32 can be detached from the taper section 62. Accordingly, an operation for detaching the damaged water supply tube 31a from the insertion section 3 and replacing the tube 31a with a new water supply tube 31 can be carried out promptly, easily without the need to replace the water supply tube 31b with a new tube.

Likewise, if the water supply tube 31b is damaged, only the parts for connecting the water supply tube 31b to the connection mouthpiece 61 may be replaced with new ones without the need to replace the water supply tube 31a with a new tube.

A connection ring 67 connecting the universal cord 4 is fixed to a frame 66 in the operation section 2 by a small screw 68, and the water supply tube 31b is curved within the operation section 2 and inserted into the universal cord 4 through the connection ring 67. The radius of curvature R of the curve portion of the water supply tube 31b within the operation section 2 is set to be 17 mm or more, to thereby prevent the water supply tube 31b from being crushed.

The water supply tubes 31a and 31b in this embodiment have an inside diameter ⌀ of about 1.5 mm to provide an overall length of about 4000 mm as already described above. When water is supplied using the syringe 55, the adapter tube 50 made of a silicon tube is employed. If the tube 50 has an inside diameter ⌀ of about 1.2 mm and a length of about 300 mm, the capacity of the conduit of the water supply tubes 31a and 31b is about 7.1 cc. Even if a syringe 55 having a capacity of, for example, 10 cc is employed, water can be surely supplied by one operation. Besides, a time lag which may occur between a time when water supply starts and a time when water is actually fed is advantageously small.

If water is supplied using the water supply pump unit 24 and the quantity of water supplied by the water supply pump unit 24 increases, pressure increases and the adapter tube 50 made of a silicon tube expands. Due to this, it takes a time until the expanded tube goes down even if the switch of the unit 24 is turned off, with the result that a time lag occurs between a time when the switch is turned off and a time when the supply of water is finished. Since the water supply pump unit 24 is a roller pump, it is necessary that the supply tube 56 has elasticity to a certain extent.

Considering this, in this embodiment, the hard, thick adapter tube 50 having an inside diameter ⌀ of about 2.5 mm, a thickness of about 3 mm, a length of about 1200 mm, a rubber hardness (JIS A hardness) of 70 degrees is employed. Since the adapter tube 50 is hard and thick, it is not expanded even if water supply pressure increases. Thus, the above-stated time lag does not occur.

Further, if taking the effective length of the insertion section 3 of the endoscope 1 and the specification of the outside diameter thereof into consideration, the lengths and inside diameters of the water supply tubes 31a and 31b vary. Namely, by appropriately selecting the adapter tube 50 depending on the type of the endoscope 1 to be used and depending on how to supply water (by the syringe 55 or by the water supply pump unit 24), it is possible to obtain good operativity.

Figure 9:
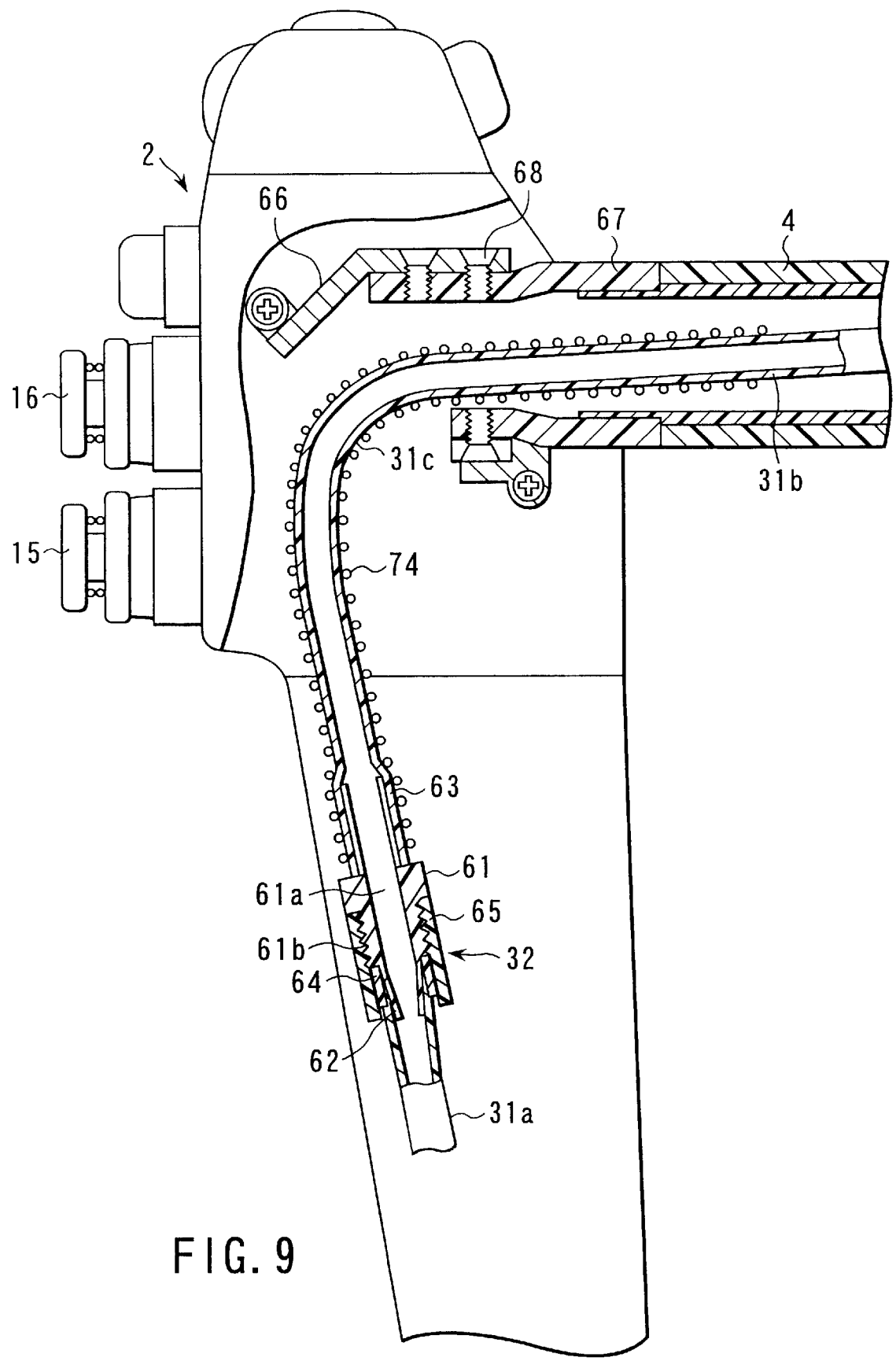
FIG. 9 is a side view of the partly cut operation section of an endoscope according to the second embodiment of the present invention.

FIG. 9 shows the second embodiment of the present invention. In various embodiments described below, the same members as those in the first embodiments are denoted by the same reference symbols, the description of which will not be given herein.

The second embodiment comprises the reinforcement structure of a water supply tube 31b within an operation section 2. A coil 74 is wound around the curved section 31c of the water supply tube 31b connected to a water supply tube 31a by a connection member 32. This can prevent the water supply tube 31b from being crushed on the curved portion 31c and prevent the tubes from being damaged due to the interference of the tubes with other members. If the connection member 32 connected to the water supply tube 31a is provided in the vicinity of the interior of a connection ring 67 within the operation section 2, the water supply tube 31a has a curved portion. If so, it suffices to wind a coil 74 around the water supply tube 31a. The coil 74 may be a close-coiled helical spring obtained by closely adjoining adjacent wires to each other.

Figure 10:
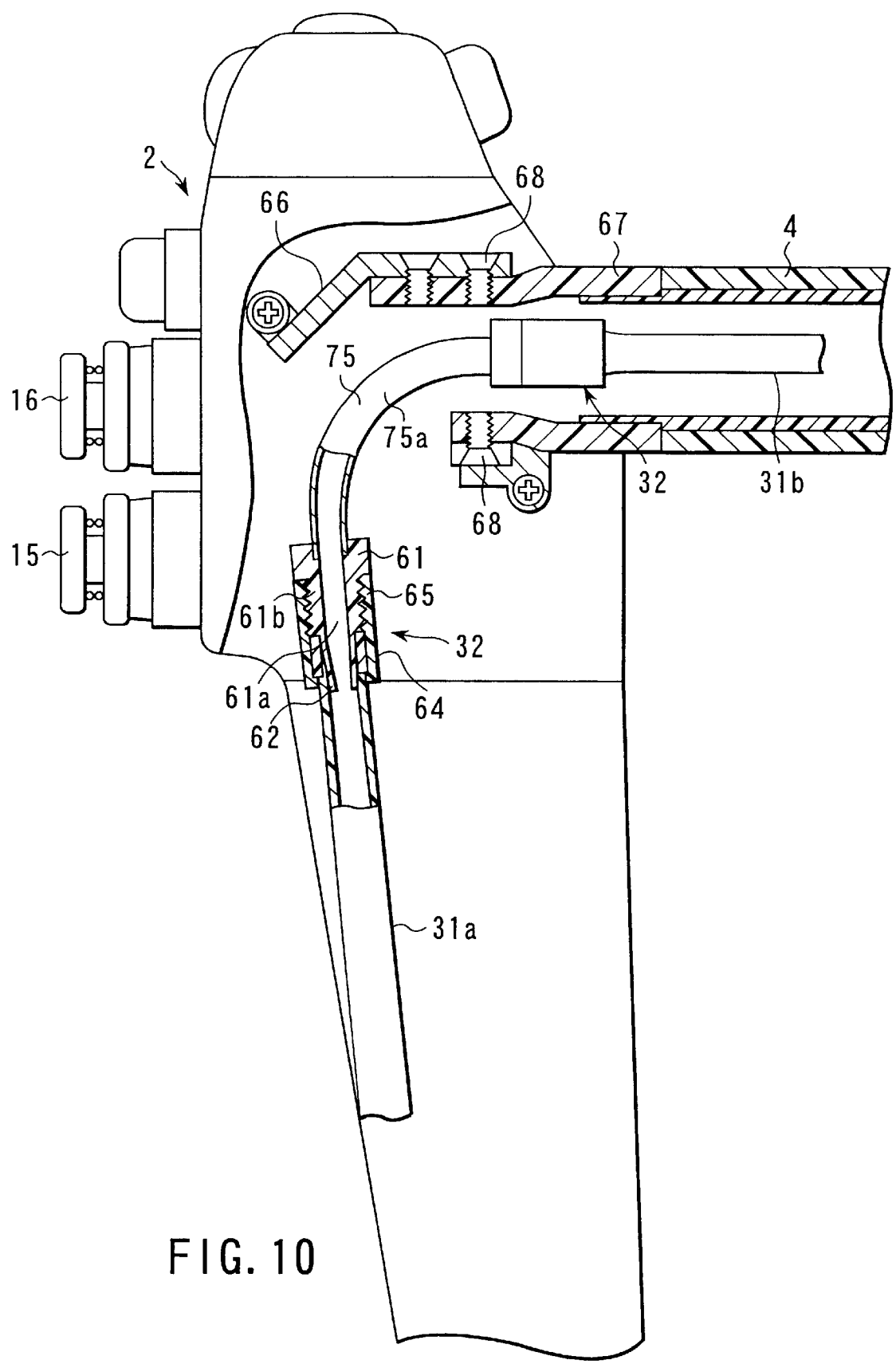
FIG. 10 is a side view of the partly cut operation section of an endoscope according to the third embodiment of the present invention.

FIG. 10 shows the third embodiment of the present invention. The same members as those in the first embodiment are denoted by the same reference symbols, the description of which members will not be given herein. In this embodiment, a rigid pipe 75 having a curved portion 75a within an operation section 2 is provided, one end portion of the rigid pipe 75 is connected to a water supply tube 31a through a connection member 32 and the other end portion thereof is connected to a water supply tube 31b through the connection member 32. It is not, therefore, necessary to bend the water supply tube 31b, thereby making it possible to prevent the tube from being flatten or crushed and to prevent the tubes from being damaged due to the interference of the tubes with other members. The rigid pipe 75 is either a metallic pipe or a synthetic resin pipe and is almost the same in inside diameter as the water supply tubes 31a and 31b.

Figure 11:
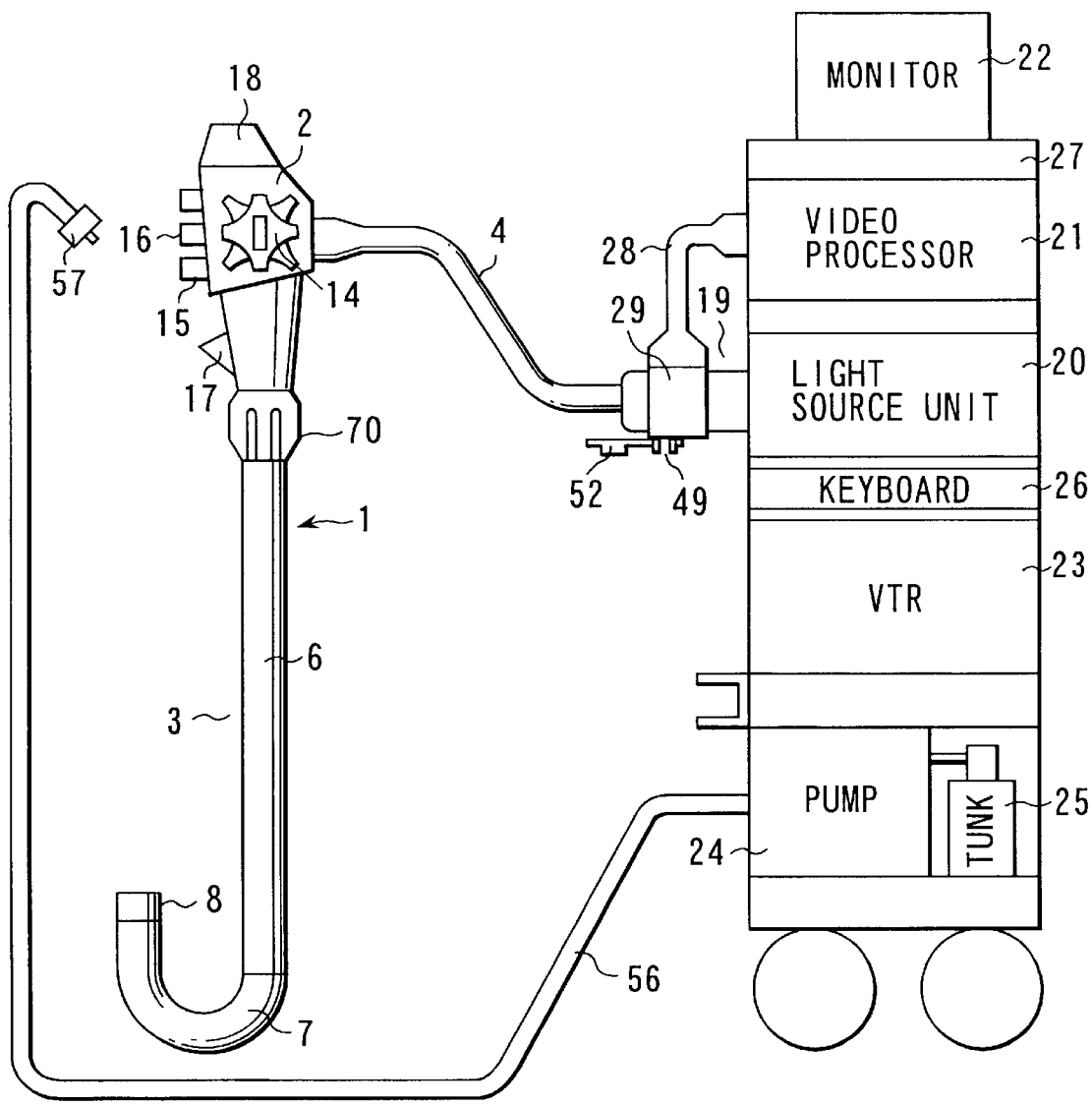
FIG. 11 is an explanatory view for schematically showing the overall constitution of an endoscope system according to a modification.

An endoscope system according to a modification shown in FIG. 11 has a rigidity varying knob 70 capable of varying the rigidity of an insertion section 3 provided on the operation section of an endoscope 1. Also, a water supply pump unit 24 has a water supply quantity varying function. A long supply tube 56 is connected to the water supply pump unit 24. An inserted connector 57 on the distal end portion of the supply tube 56 can be connected to the insertion port 17 of the endoscope 1 to thereby allow water to be supplied from a distal end opening 12 through a treatment tool insertion channel. The treatment tool insertion channel has a larger bore than those of the water supply tubes 31a and 31b, so that the water supply quantity of the water supply pump unit 24 can be increased.

Figure 12:
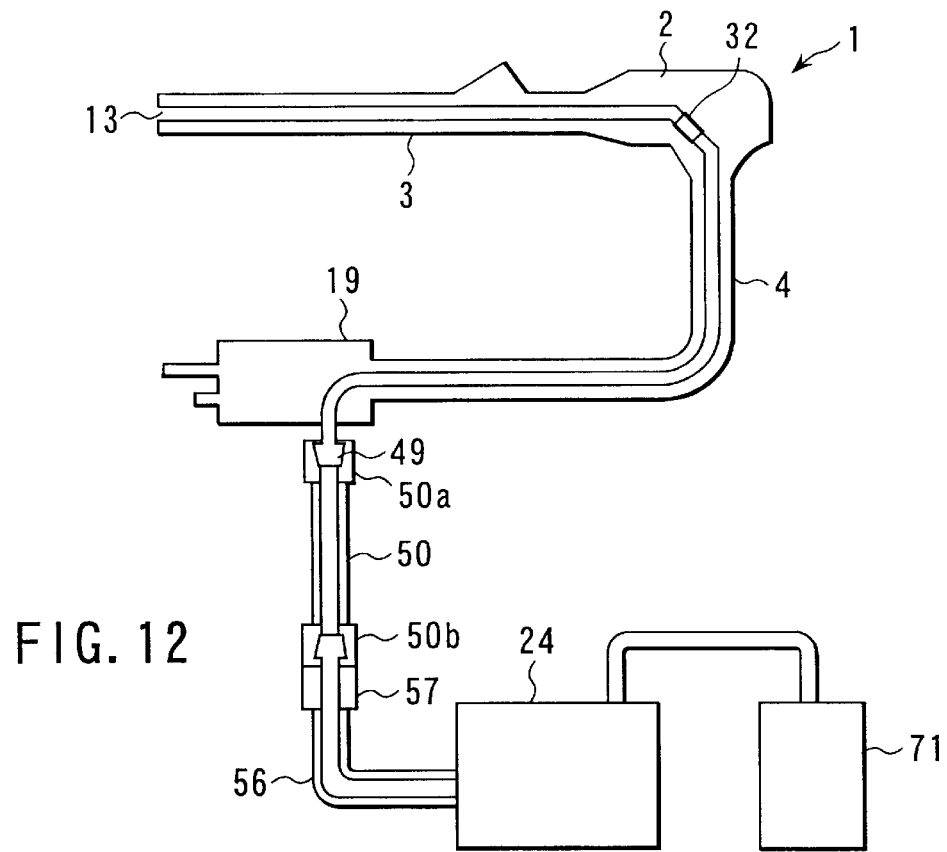
FIG. 12 is a schematic block diagram showing the forward water supply conduit of an endoscope system according to another modification.

In an endoscope system according to another modification shown in FIG. 12, a commercially available sterilized water pack 71 instead of a water tank 25 is connected to a water supply pump unit 24 to thereby allow sterilized water to be supplied by the water supply pump unit 24 from a forward water supply port 13 through water supply tubes 31a and 31b.

Figure 13:
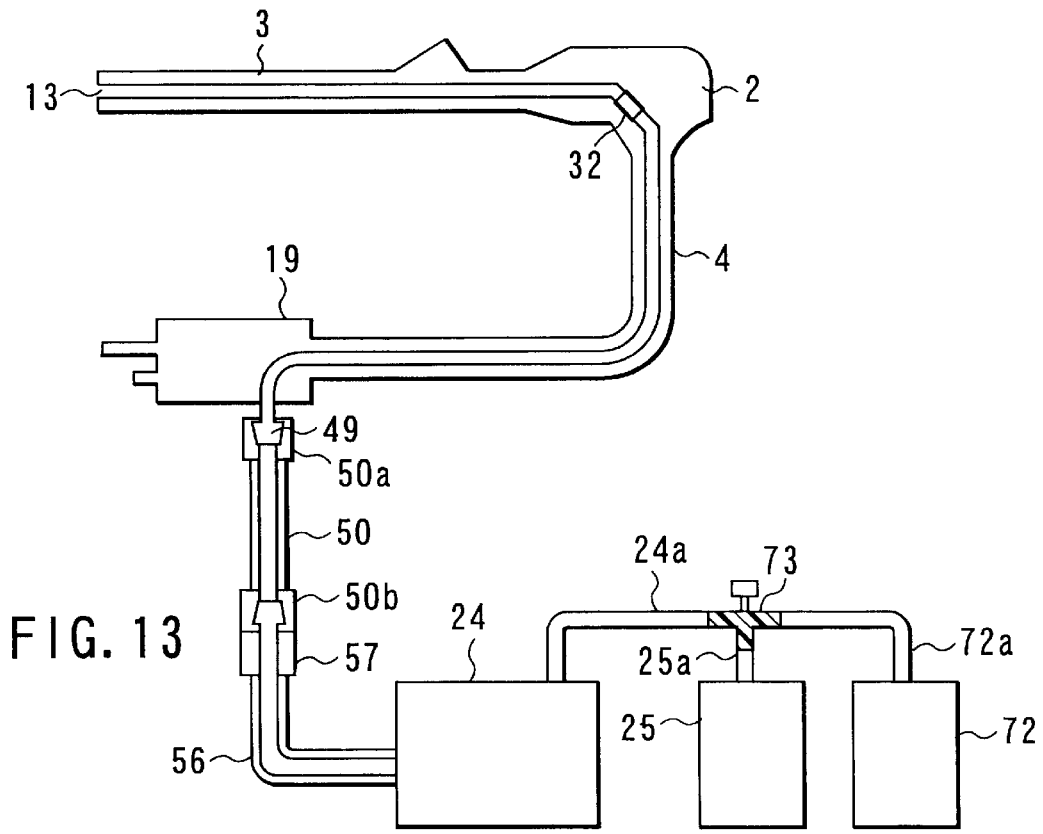
FIG. 13 is a schematic block diagram showing the forward water supply conduit of an endoscope system according to yet another modification.

In an endoscope system according to yet another modification shown in FIG. 13, a conduit 24a connected to a water supply pump unit 24, a conduit 25a connected to either a water tank 25 or a sterilized water pack 71 and a conduit 72a connected to a pigment tank 72 are connected to one another through a three-way selector valve 73 to thereby allow switching over water (or sterilized water) to/from pigment.

Figure 14:
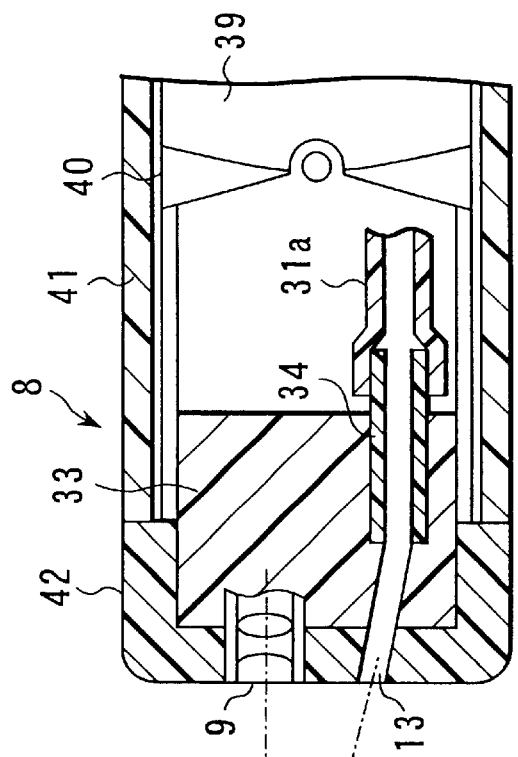
FIG. 14 is a longitudinal side view showing a modification of the distal end portion of the endoscope.

FIG. 14 shows a modification of the internal structure of the distal end portion 8 of an endoscope. A forward water supply port 13 connected to the distal end portion of a water supply tube 31a through a pipe 34 is bent in the direction of the optical axis of an observation window 9. If the forward water supply port 13 is constituted as stated above, water supplied from the forward water supply port 13 is supplied toward the central portion of the field of view of an observation optical system. Due to this, it is possible to advantageously check a water supply state while an affected part is being observed.

Figure 15:
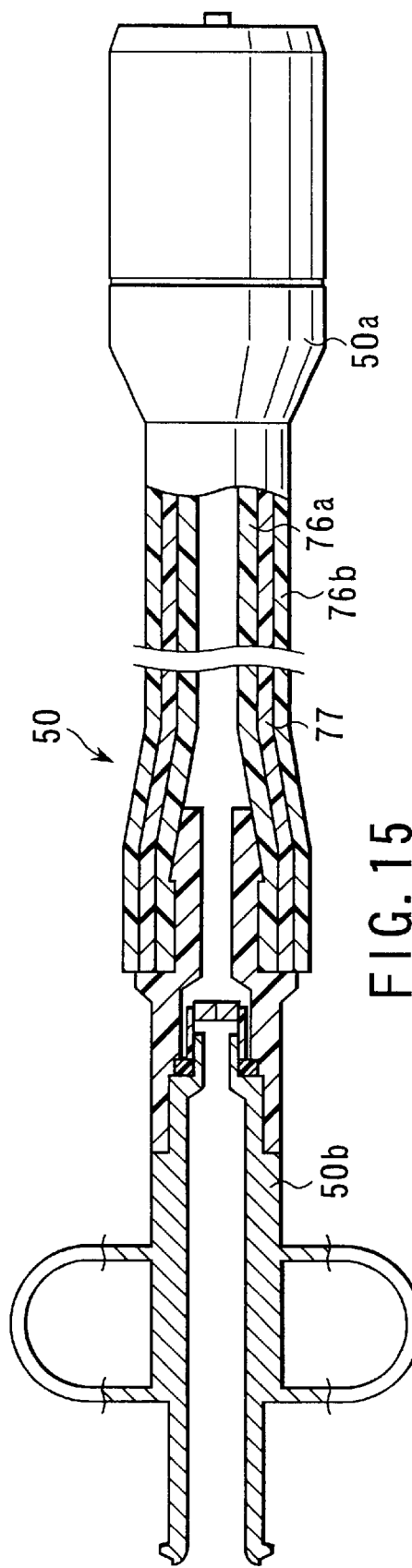
FIG. 15 is a longitudinal side view of an adapter tube according to a modification.

FIG. 15 shows a modification of an adapter tube 50 connecting a water supply pump unit 24 to a mouthpiece 49. The adapter tube 50 is formed to have a three-layer structure in which a blade 77 is interposed between an inner tube 76a and an outer tube 76b. With the adapter tube 50 thus constituted, even if the water supply pressure of the forward water supply pump 24 is high, the adapter tube 50 does not expand and the above-stated time lag can be, therefore, advantageously avoided.

FIG. 16A shows a modification of the operation section 2 of an endoscope. A rigidity varying knob 70 for varying the rigidity of an insertion section 3 is rotatably provided on the operation section 2. Numbers 78 from "1", "2", . . . are allotted to the rigidity varying knob 70 in circumferential direction. The rigidity of the insertion section 3 can be set by rotating the rigidity varying knob 70 and adjusting one of the numbers 78 to an index 79 provided on the outer wall of the operation section 2. The higher the number adjusted to the index 79, the higher the rigidity of the insertion section 3 becomes. This index may be freely selected such as an index which indicates not a number but a position. The direction of rotation is determined based on human engineering. An operator can increase the rigidity of the operation section 3 by conducting a rotation operation in the same direction as that in which the operator increases the volume of a radio.

Further, the intervals of the numbers 78 are uniform and the positions of the operation section during rotation can be easily recognized. Indexes may be allotted at these intervals in accordance with the quantity of change in the rigidity of the insertion section 3 while the quantity of change is set constant. In this case, since the positions of the indexes 79 indicate the rigidity of the insertion section 3, the operator can advantageously recognizes which position in the range of the rigidity of the insertion section 3 the rigidity of the insertion section corresponds. Accordingly, the operator can intuitively see the direction in which rigidity increases and does not erroneously rotate the operation section inversely, thereby greatly improving operativity. Further, since the occurrence of operation errors is reduced, it is possible to prevent the waste of check time and to make an efficient check. Besides, since the occurrence of operation errors is reduced, the possibility that the operator erroneously makes the insertion section 3 rigid though the operator intends to make the insertion section 3 softer is reduced.

As shown in FIG. 16B, each number 78 may be displayed by a convex part at the bottom of a circular concave portion 80 so that the number 78 can be discerned by touching the number with fingers. Alternatively, as shown in FIG. 16C, the number 78 may be displayed by a concave part at the bottom of a circular concave portion 80. Alternatively, a fluorescent paint may be applied to the bottom of the concave portion 80 or the convex or concave portion by which the number 78 is displayed so that the position of the number 78 can be easily checked even in the dark and operativity can be improved.

Figure 17:
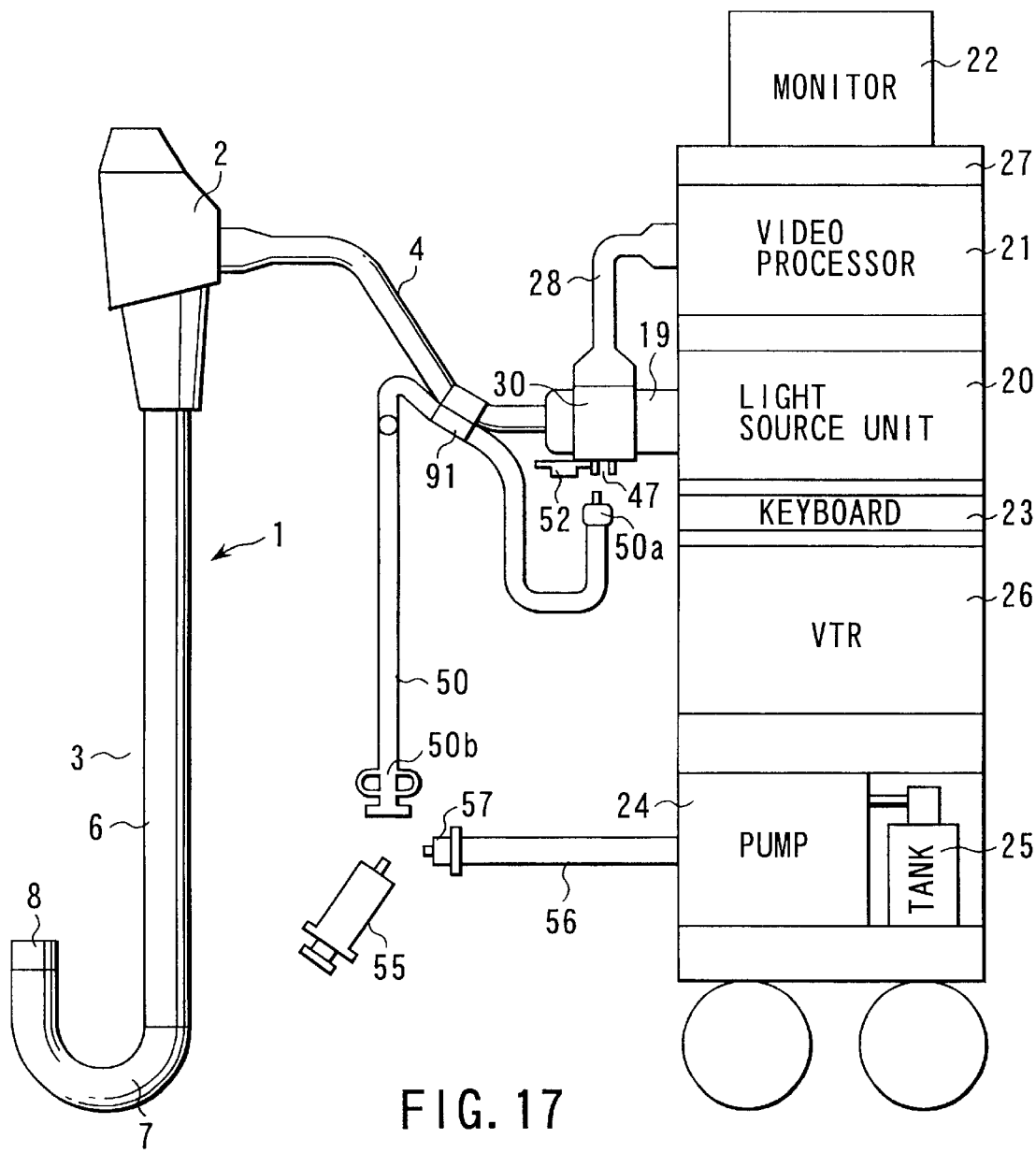
FIG. 17 is an explanatory view for schematically showing the overall constitution of an endoscope system according to yet another modification.
Figure 18A:
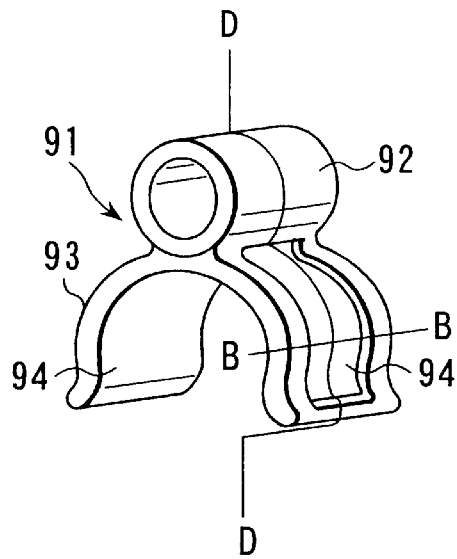
FIG. 18A is a perspective view of a binding clip used in the endoscope system shown in FIG. 17.
Figure 18B:
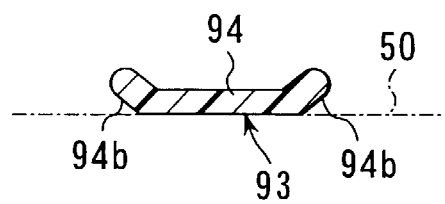
FIG. 18B is a cross-sectional view taken along line B—B of FIG. 18A.
Figure 18C:
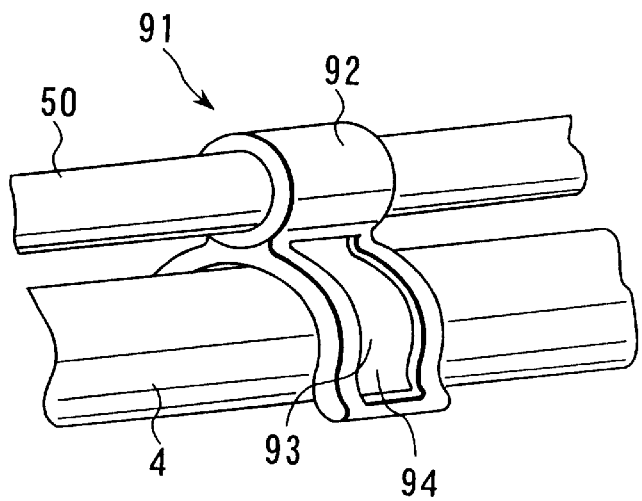
FIG. 18C is a perspective view showing a state in which the binding clip is used and FIG. 18D is a cross-sectional view taken along line D—D of FIG. 18A.
Figure 18D:
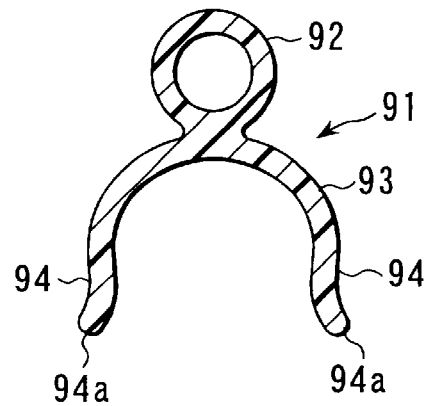

In an endoscope system according to yet another modification shown in FIGS. 17 to 18D, an adapter tube 50 and the universal cord 4 of an endoscope 1 are bound by a fingertip binding clip 91. This binding clip 91 has the cylindrical first holding section 92 fitted into the adapter tube 50 and the second holding section 93 into which the universal cord 4 is fitted to be elastically held by the second holding section 93, as shown in FIGS. 18A to 18D. The first holding section 92 is integrally coupled to the back of the second holding section 93.

A bent portion 94a bent externally is provided on the distal end portion of each of the both legs 94 of the second holding section 93 and a curved portion 94b curved externally is provided on the outer peripheral edge of each leg 94. Therefore, when the second holding section 93 is fitted onto the universal cord 4, the bent portions 94a become fitting guides. After fitting the second holding section 93 onto the universal cord 4, the bent portions 94b allow the second holding section 98 to separate from the surface of the universal cord 4. Thus, even if the universal cord 4 is swung, it is advantageously possible to prevent the cord 4 from being easily scratched.

Furthermore, if the adapter tube 50 is bound with the universal cord 4 of the endoscope 1 using the binding clip 91, the adapter tube 50 does not sway to and fro and does not get in the way while being operated during a check or while the endoscope 1 is carried from a checkup room to a cleaning room.

Figure 19:
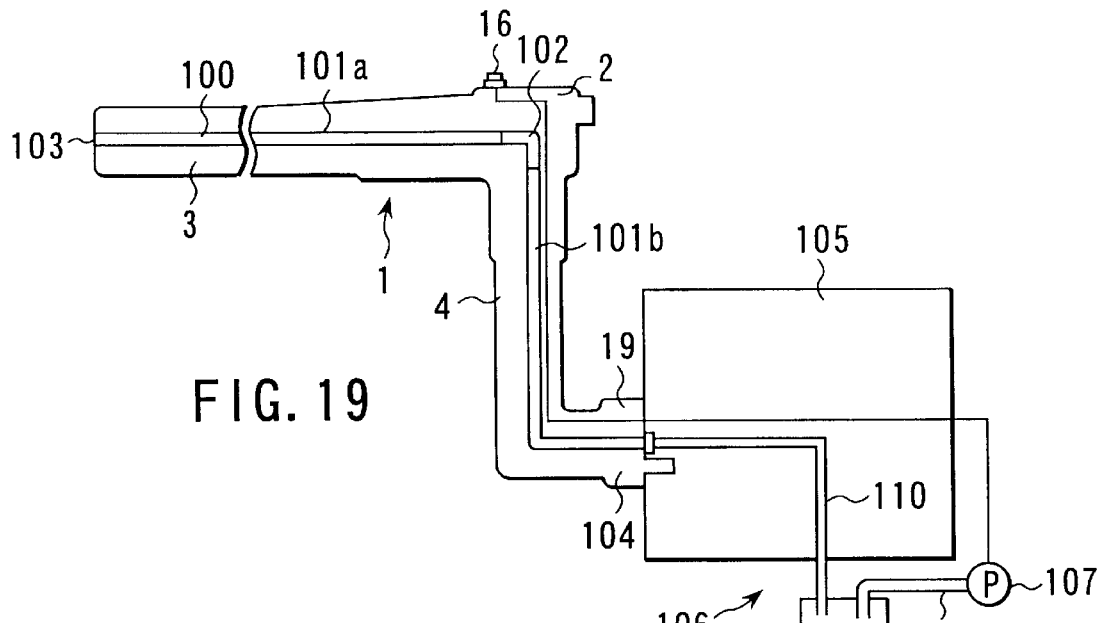
FIG. 19 is a schematic block diagram of an endoscope system provided with a suction system according to the fourth embodiment of the present invention.

FIG. 19 shows an endoscope system according to the fourth embodiment of the present invention. This endoscope system comprises an endoscope suction unit schematically shown therein.

An endoscope 1 according to this embodiment is provided with a suction conduit 100 communicating with a universal cord 4 through an insertion section 3 from an operation section 2. The suction conduit 100 is constituted such that a suction tube 101a and a universal cord 101b are connected to each other by a connection section 102 within the operation section 2. The distal end portion of the suction tube 101a is connected to the suction port 103 of a distal end portion 8 and the distal end portion of the suction tube 101b is connected to the suction connector 104 of a connector 19.

The connector 19 is connected to a control unit 105. The control unit 105 is connected to a suction unit 106. The suction unit 106 consists of a suction pump 107 turned on and off by the suction operation button 16 of the operation section and a suction tank 109 communicating with the suction pump 107 through a suction pipe 108. The suction tank 109 is connected to a suction tube 101b through a suction tube 110.

With the above-stated system, if the suction operation button 16 is turned on to drive the suction pump 107, the pressure of the suction tank 109 becomes negative through the suction pipe 108 and the pressures of the suction tubes 101a and 101b become negative. Due to this, mucus in the body cavity is sucked from the suction port 103 into the suction tank 109 through the suction tubes 101a and 101b and the mucus can be stored in the suction tank 109.

In addition, while the suction tube 101a is extended in the insertion section 3 and the suction tube 101b is extended in the universal cord 4 during the assembly of the endoscope 1, these suction tubes 101a and 101b can be connected to each other, in a detachable manner, through the connection section 102 within the operation section 2. Therefore, during the assembly of the endoscope 1, it is possible to prevent the long suction tubes 101a and 101b from being pulled out of the endoscope 1 and entangled with each other and from interfering with other members, thereby improving assembly operativity.

Furthermore, if the endoscope 1 is used for a long time and one or both of the suction tubes 101a and 101b are damaged and needed to be replaced with new tubes, the suction tubes 101a and 101b are divided at the connection section 102 of the operation section 2. By doing so, an operation for pulling out only the damaged suction tube 101a or 101b from the insertion section 3 or the universal cord 4 and for replacing the damaged tube with a new suction tube 101a or 101b can be advantageously carried out in a short time.

Figure 20:
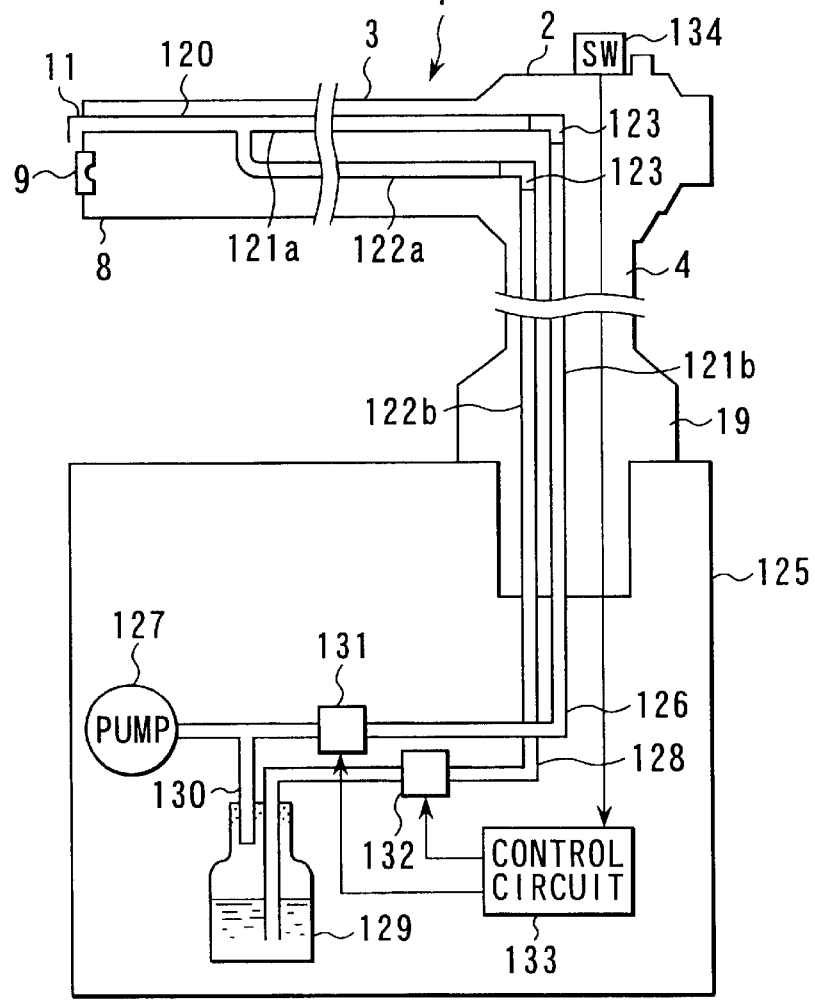
FIG. 20 is a block diagram showing the overall constitution of an endoscope system provided with an endoscope air/water supply system according to the fifth embodiment of the present invention.

FIG. 20 shows the schematic block diagram of the endoscope and the air/water supply unit of an endoscope system according to the fifth embodiment of the present invention. A nozzle 11 provided on the distal end portion 8 of the endoscope 1 is connected to an air/water supply tube 120 included in an insertion section 3. The air/water supply tube 120 has two conduits by separating an air supply tube 121a and a water supply tube 122a in the middle of the insertion section 3. The air supply tube 121a and the water supply tube 122*a* are connected to an air supply tube 121*b* and a water supply tube 122*b* through a connection section 123 within an operation section 2, respectively and extended in a universal cord 4.

The connector 19 of the universal cord 4 is connected to an air/water supply unit 125. The air supply tube 121*b* is connected to an air supply pump 127 through an air supply conduit 126 within the air/water supply unit 125. The water supply tube 122*b* is connected to a water supply tank 129 through a water supply conduit 128 within the air/water supply unit 125.

The air supply conduit 126 is connected, in a dividable manner, to a water supply pressurized conduit 130. This water supply pressurized conduit 130 is communicated with and connected to a space above the level of a stored fluid within the water supply tank 129. Further, the first solenoid valve 131 is provided on the air supply conduit 126 and the second solenoid valve 132 is provided on the water supply conduit 128. The first solenoid valve 131 and the second solenoid valve 132 are connected to an air/water supply switch 134 provided on the operation section 2 through a control circuit 133.

With the above-stated system, the air/water supply switch 134 is operated, whereby the first and second solenoid valves 131 and 132 can be turned on and off and water can be supplied from the nozzle 11 toward an observation window 9 through the water supply tubes 122*a* and 122*b* and the air/water supply tube 120. Further, after supplying water, air is supplied from the nozzle 11 toward the observation window 9 through the air supply tubes 121*a* and 121*b* and the air/water supply tube 120, whereby moisture or water attached to the observation window 9 can be blown off.

While the air supply tube 121*a* and the water supply tube 122*a* are extended in the insertion section 3 and the air supply tube 121*b* and the water supply tube 122*b* are extended in the universal cord 4 during the assembly of the endoscope 1, the air supply tubes 121*a*, 121*b* and the water supply tubes 122*a*, 122*b* can be connected to one another, in a detachable manner, through the connection section 123 within the operation section 2. By doing so, during the assembly of the endoscope 1, it is possible to prevent the long air supply tube 121 and water supply tube 122 from being pulled out and entangled with each other and from interfering with other members, thereby improving assembly operativity.

Moreover, if the endoscope 1 is used for a long time and the air supply tubes 121*a*, 121*b* and the water supply tubes 122*a* and 122*b* are damaged and needed to be replaced with new tubes, the operation section 2 may be opened and the tubes may be divided at the connection section 123. By doing so, the air supply tubes 121*a*, 121*b* and the water supply tubes 122*a* and 122*b* can be pulled out from the insertion section 3 and the universal cord 4. Accordingly, an operation for pulling out the damaged air supply tube 121 and water supply tube 122 from the insertion section 3 and the universal cord 4 and for replacing them with a new air supply tube 121 and a new water supply tube 122, can be advantageously carried out promptly, easily.

Figure 21:
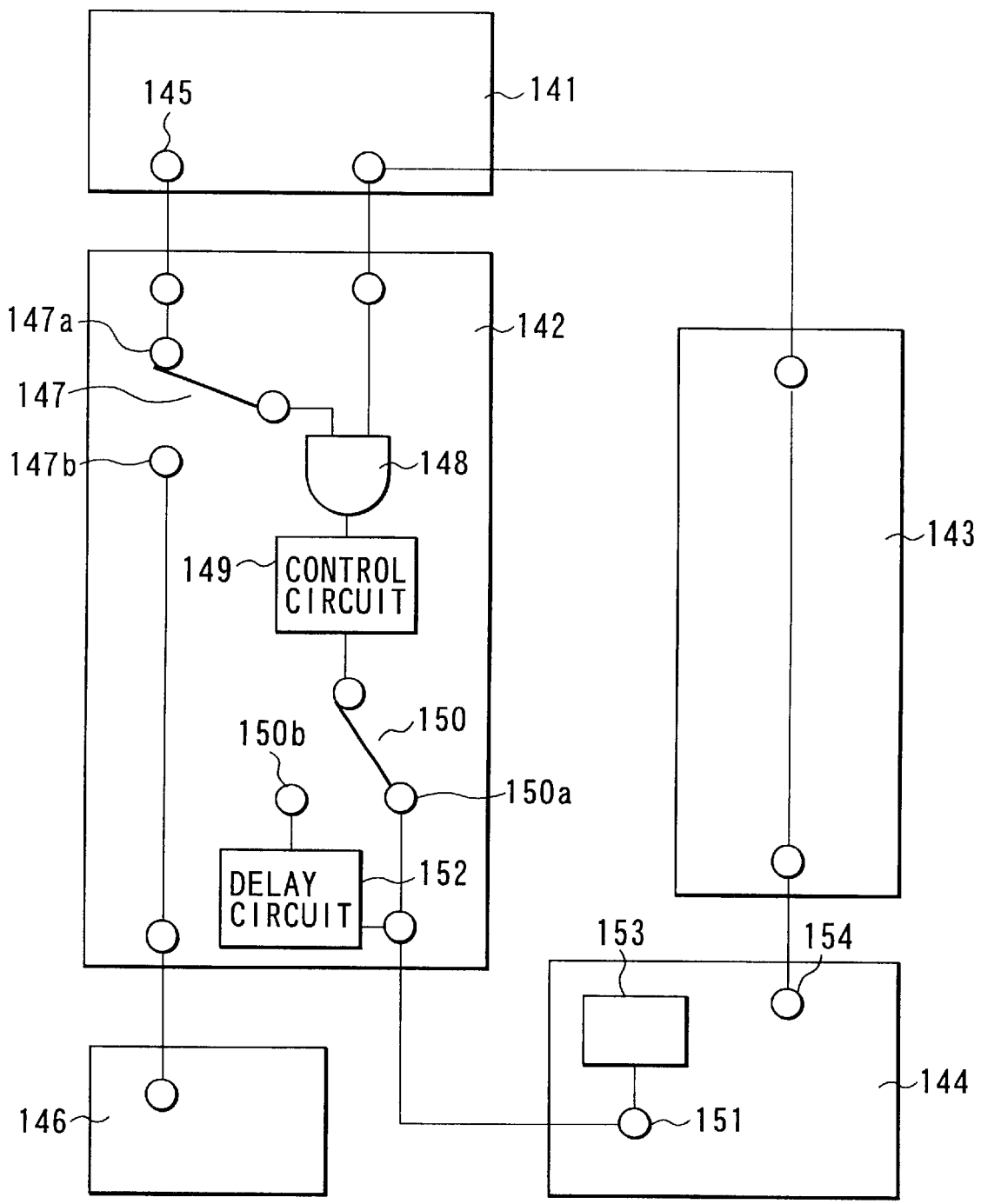
FIG. 21 is a block diagram of a water supply system according to a preferred embodiment applicable to the endoscope system.

FIG. 21 is a block diagram of an endoscope water supply system. Reference symbol 141 denotes an endoscope, 142 denotes a video processor, 143 denotes a water supply tube, and 144 denotes a water supply pump. The endoscope 141 is provided with a scope switch 145. The video processor 142 is provided with a foot switch 146.

The electrical contact of the scope switch 145 is connected to one electrical contact 147*a* of the first change-over switch 147 and the electrical contact of the foot switch 146 is connected to the other electrical contact 147*b* of the first change-over switch 147. The first change-over switch 147 is connected to one input terminal of an AND circuit 147 and the signal line of a water supply tube 143 is connected to the other input terminal of the AND circuit 148 through the endoscope 141.

The AND circuit 148 is connected to the second change-over switch 150 through a control circuit 149. One electrical contact 150*a* of the second change-over switch 150 is directly connected to the pump switch 151 of a water supply pump 144 and the other electrical contact 150*b* is connected to the pump switch 151 through a delay circuit 152. In addition, when the pump switch 151 is turned on, the water supply pump 144 is driven through a pump driving circuit (not shown) and a sound source 153, such as a buzzer, generating sound is connected to the pump switch 151. The water supply pump 144 is provided with a sensor 154 sensing whether or not the water supply tube 143 is surely connected to the water supply pump 144.

Accordingly, using the first change-over switch 148, it is possible to use either the scope switch 145 or the foot switch 146 by changing over the scope switch 145 to/from the foot switch 146. When the water supply tube 143 is surely connected to the water supply pump 144 and the scope switch 145 or the foot switch 146 is turned on, the water supply pump 144 is driven to thereby make it possible to prevent the water supply pump 144 from being driven before the water supply tube 143 is surely connected to the water supply pump 144 and to prevent water leakage.

Further, using the second change-over switch, it is possible to select whether the water supply pump 144 is driven simultaneously when the switch is turned on or the water supply pump 144 is driven after a certain time (several seconds) of turning the switch on. Furthermore, if the pump switch 151 is turned on, sound is generated from the sound source 153, whereby it is possible to sense by the sound that the water supply pump 144 is driven.

It is also possible to set the pump switch 151 such that if the scope switch 145 and the foot switch 146 are kept depressed, the pump switch 151 is turned on and that if the scope switch 145 and the foot switch 146 are not depressed, the pump switch 151 is turned off. Further, by making the quantity of water supplied by the water supply pump 144 variable, the quantity of supplied water can be appropriately adjusted in accordance with the inside diameters of the conduits of the water supply tube 143 and the endoscope 141.

Figure 22:
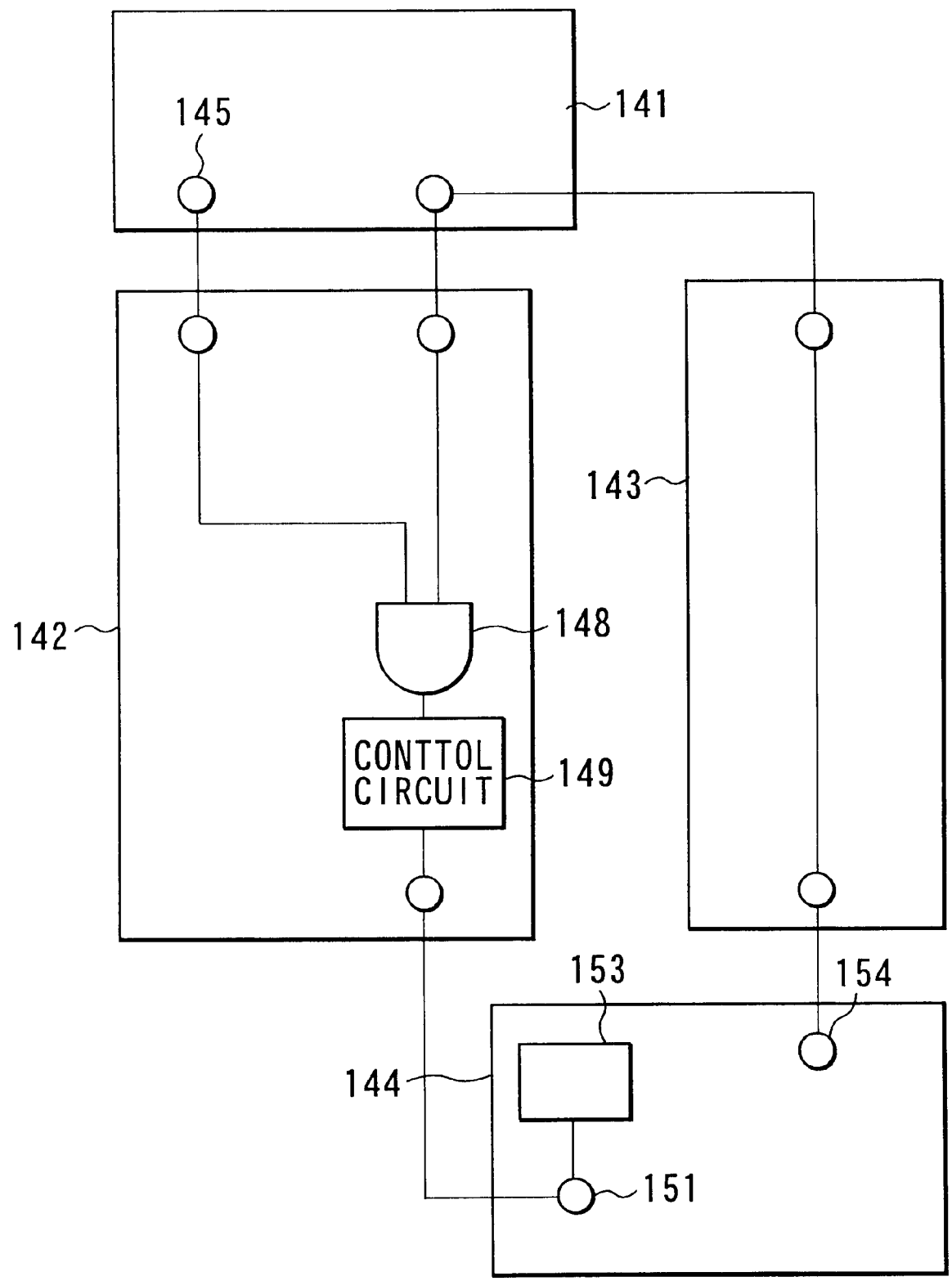
FIG. 22 is a block diagram of a water supply system according to another embodiment applicable to the endoscope system.

FIG. 22 is a block diagram of an endoscope water supply system. The endoscope water supply system shown in FIG. 22 is basically the same as the system shown in FIG. 21. Namely, a pump switch 151 is turned on and off only by a scope switch 145. In this system as in the case of the system shown in FIG. 21, when a water supply tube 143 is surely connected to a water supply pump 144 and either the scope switch 145 or a foot switch 146 is turned on, the water supply switch 144 is driven. Due to this, it is possible to prevent the water supply pump 144 from being driven before the water supply tube 143 is surely connected to the water supply pump 144 and to prevent water leakage.

Figure 23:
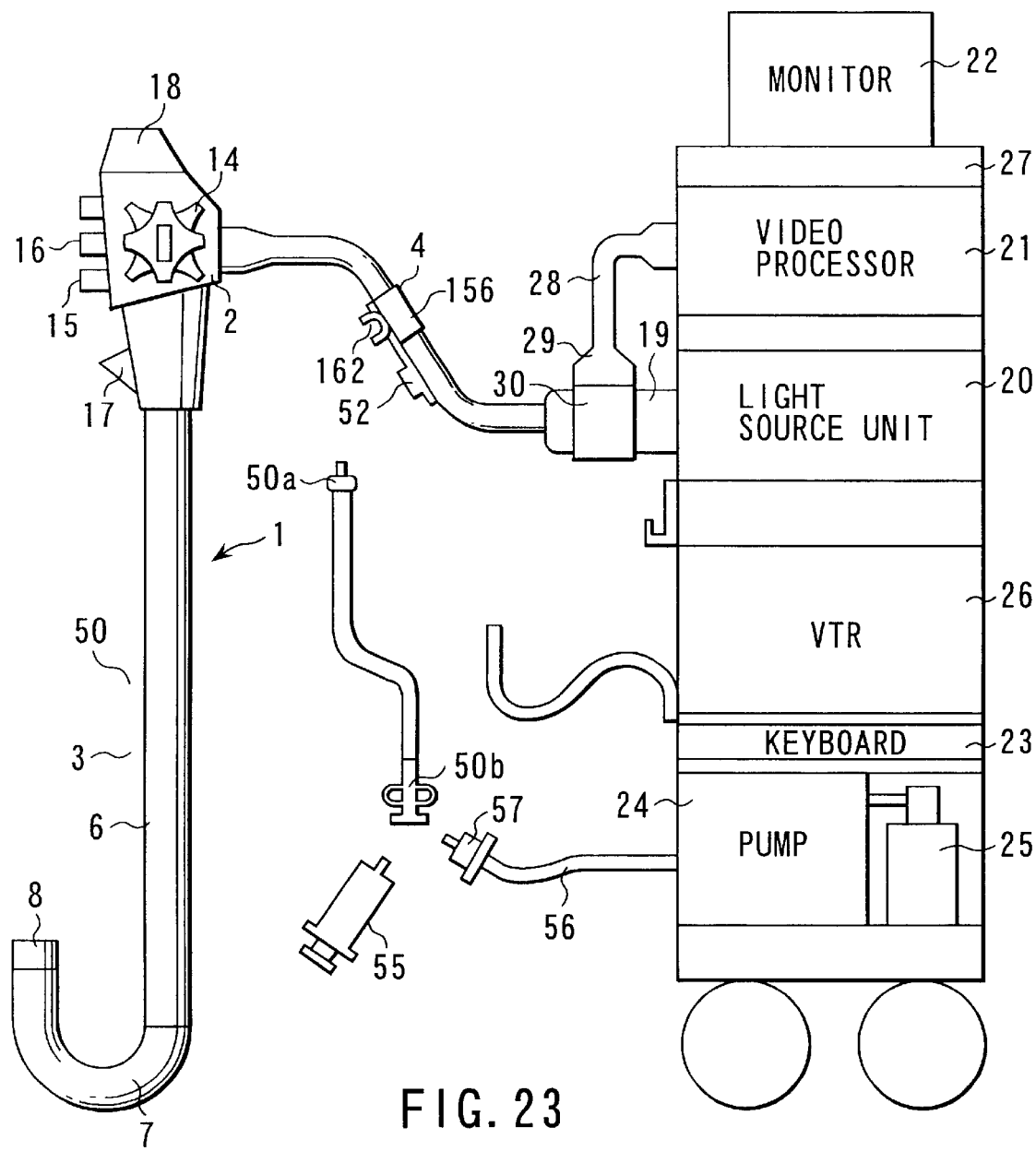
FIG. 23 is an explanatory view for schematically showing the overall constitution of an endoscope system according to the sixth embodiment of the present invention.
Figure 24:
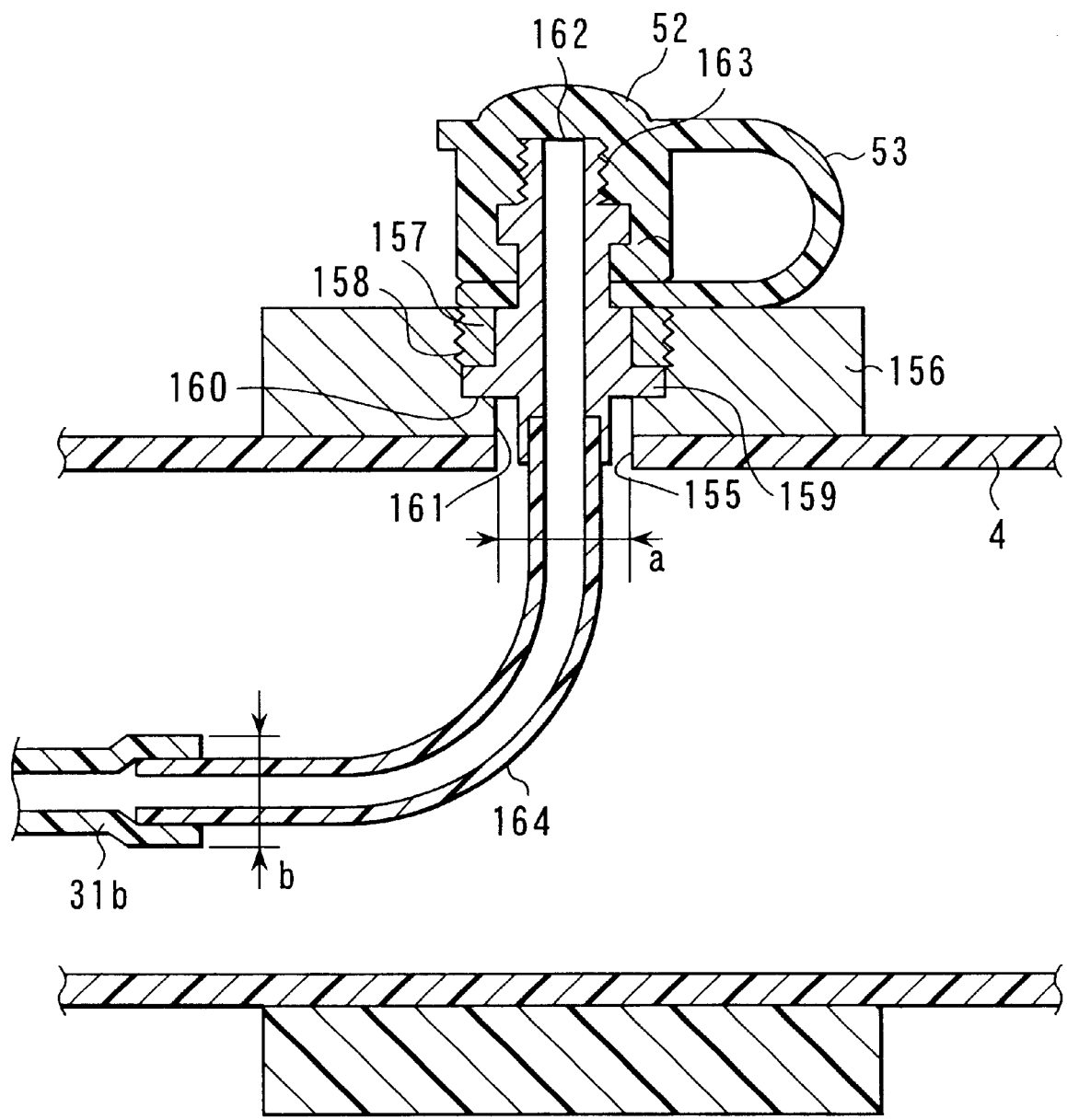
FIG. 24 is a cross-sectional view of a part of the universal cord of an endoscope shown in FIG. 23.

FIGS. 23 and 24 show an endoscope system according to the sixth embodiment of the present invention. A connector member 156 made of metal or resin is provided on a universal cord 4. The connector member 145 is provided with a male screw portion 158 with which a stopper ring 157 to be described later is screwed, a butt portion 150 against which a mouthpiece 159 to be described later is butted, and a hole 161. The inside diameter ø of the hole 161 is about 8 mm.

The connector member 156 is bonded airtight and fluid-tight to the universal cord 4 so that a hole 155 having an inside diameter ø of 8 mm and provided in the universal cord 4 and the hole 161 of the connector member 156 are almost coaxial with each other. The butt surface between the connector member 156 and the mouthpiece 159 is flat. The mouthpiece 159 is fixedly attached to the connector member 156 by butting the mouthpiece 159 against the connector member 156 and screwing the stopper ring 158 with the male screw portion 158. The stopper ring 157 holds the connector member 156 and the mouthpiece 159 airtight and fluid-tight. The mouthpiece 159 is made of metal. A water supply port 162 is provided on the exposed distal end portion of the mouthpiece 159 and a male screw portion 163 into which the first connector 50a of an adapter tube 50 is screwed and to which the first connector 50a is connected, is provided on the outer periphery of the mouthpiece 159. Further, the mouthpiece 159 penetrates the connector member 156 and the hole 155 of the universal cord 4. A hard pipe 164 is coupled to the mouthpiece 159. A water supply tube 31b connected to a water supply tube 31a within an operation section is connected to the hard pipe 164.

The diameters "a" of the hole 155 formed in the universal cord 4 and the hole 161 of the connector 156 are set to be larger than the diameter "b" of the coupling section between the hard pipe 164 and the water supply tube 31b. Therefore, when the water supply tube 31b is damaged, the supply tube 31b can be replaced with a new tube by dividing the water supply tube 31a and the water supply tube 31b connected to each other within the operation section and pulling out the hard pipe 164 and the water supply tube 31b integral with the mouthpiece 159 from the connector member 156. Since the connector member 156 and the mouthpiece of the water supply tube 31b are independent of each other, there is no need to replace the water supply tube 31a with a new tube and to disassemble the connector member 156, thereby making it possible to carry out a repair operation efficiently. Further, in this embodiment, an operator can conveniently supply water alone using a syringe 55 without preparing a long dedicated adapter tube 50 because of the mouthpiece 159 on the universal cord 4.

Figure 25:
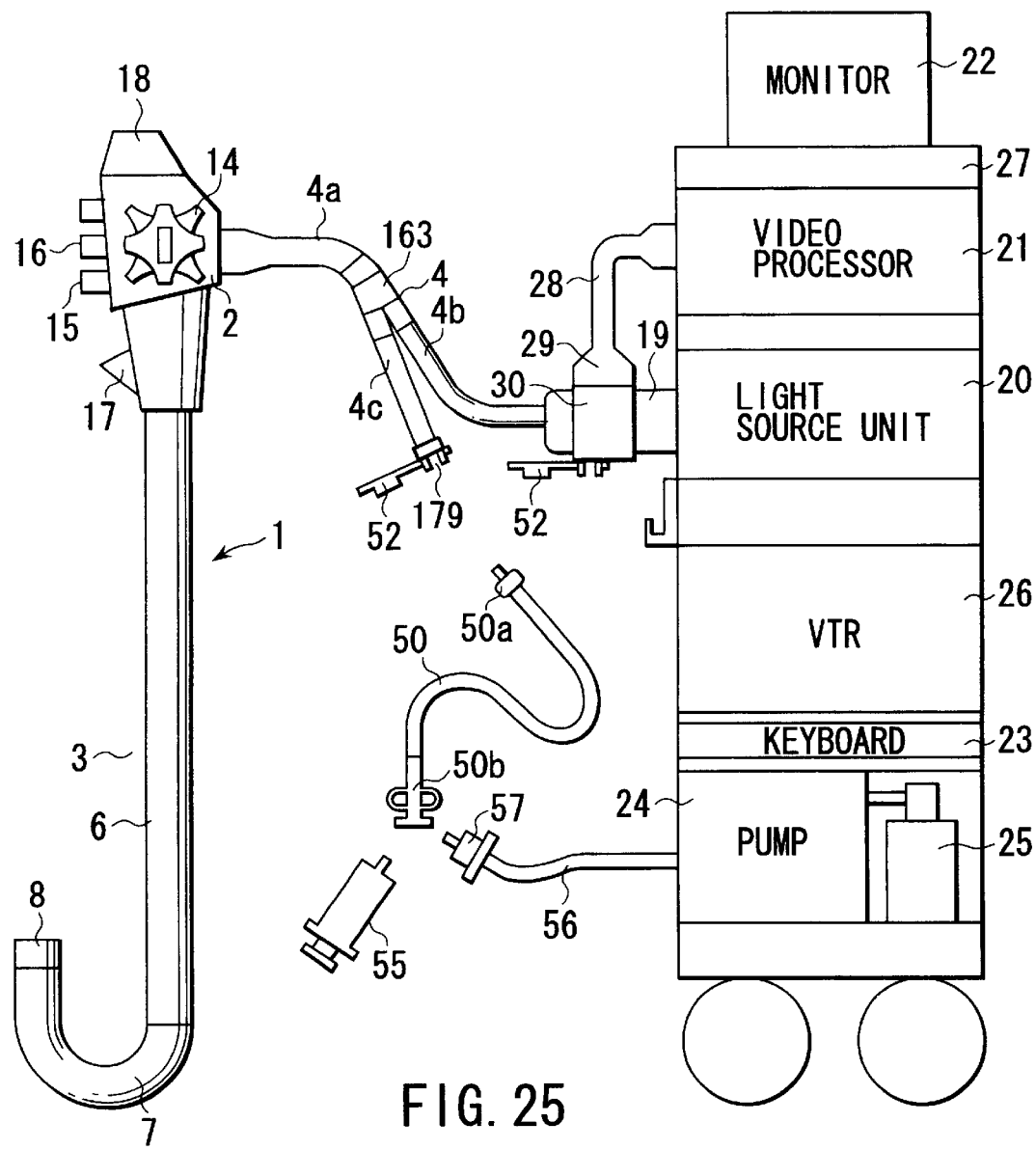
FIG. 25 is an explanatory view for schematically showing the overall constitution of an endoscope system according to the seventh embodiment of the present invention.
Figures 26, 27:
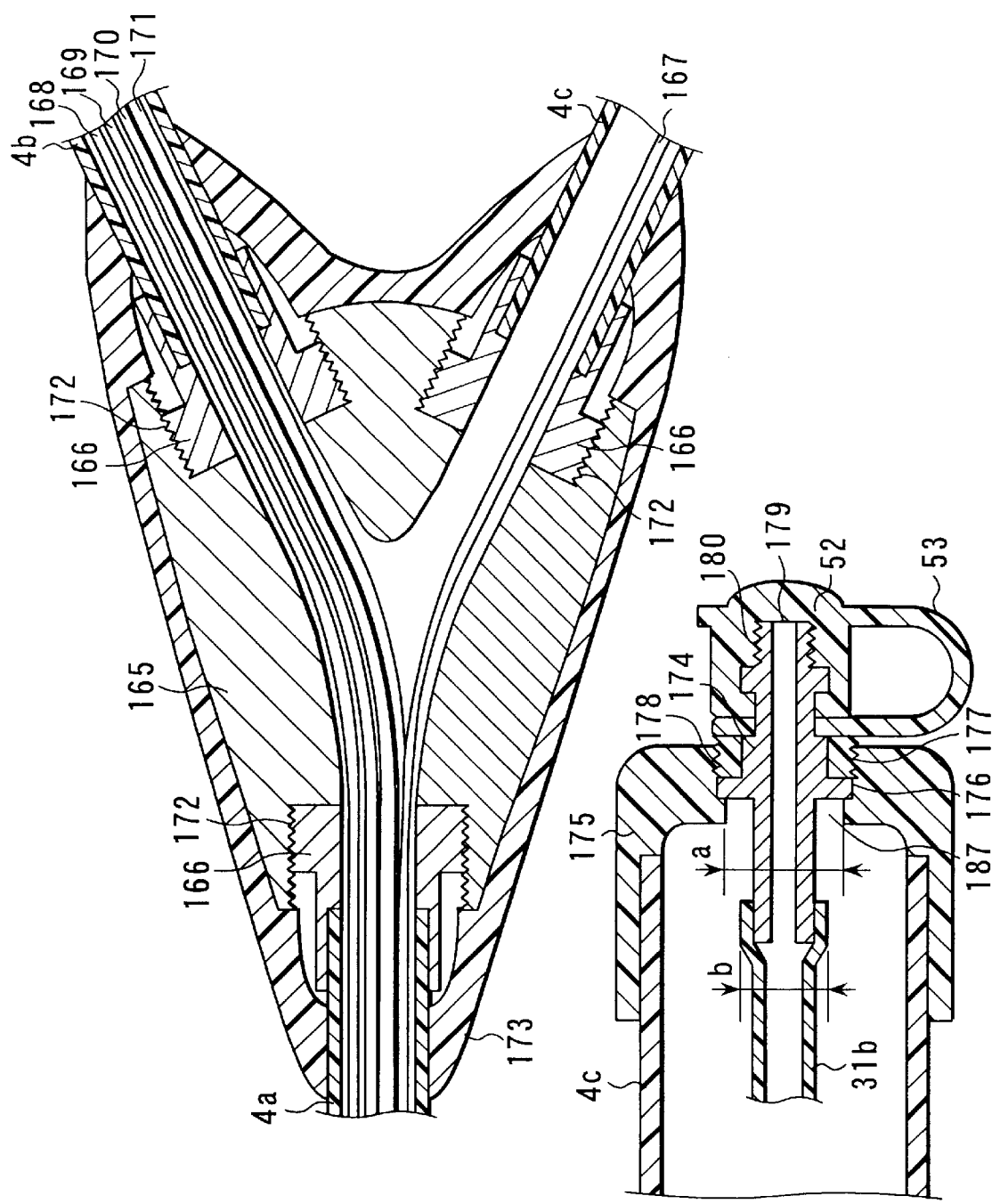
FIG. 26 is a cross-sectional view of the Y branch of an endoscope shown in FIG. 25.
FIG. 27 is a cross-sectional view of a part of the universal cord of the endoscope system shown in FIG. 25.

FIGS. 25, 26 and 27 show an endoscope system according to the seventh embodiment of the present invention. A Y branch 165 made of metal or resin is connected to the other end of a universal cord 4 connected to an operation section 2. A universal cord 4b connected to a connector section 19 and a universal cord 4c having a mouthpiece 174 for connecting an adapter tube 50 on the other end thereof are connected to the Y branch 165. Only a forward water supply tube 167 is included in the universal cord 4c, while the other constituent elements such as an air supply tube 168, a water supply tube 169, a suction channel 170 and a light guide 171 are extended in the universal cord 4b.

Mouthpieces 166 are provided on the side end portions of the Y branch 165 on the universal cords 4a, 4b and 4c sides, respectively and male screw portions 172 screwed with the Y branch 165 are provided on the outer peripheries of the respective mouthpieces 166. The universal cords 4a, 4b and 4c are screwed with the male screw portions 172 of the Y branch 165. A bending stopper rubber 173 is applied onto the outer peripheries of the connection sections between the Y branch 165 and the universal cords 4a, 4b and 4c. The bending stopper rubber 173 functions to prevent bending and, therefore, prevent defects such as buckling.

A mouthpiece 174 is attached to the other end of the universal cord 4c. The mouthpiece 174 is made of metal and fixed to a cover member 175 covering the end portion of the universal cord 4c. A butt portion 176 against which the mouthpiece 174 is butted, a hole 181 and a male screw portion 178, with which a stopper ring 177 to be described later is screwed, are provided on the central portion of the diameter of the cover member 175. By butting the mouthpiece 174 against the butt portion 176 of the cover member 175 and fastening the stopper ring 177, the cover member 175 and the mouthpiece 174 are fixed to each other. A water supply port 179 is provided on the exposed distal end portion of the mouthpiece 174 and a male screw portion 180 with which the first connector 50a of the adapter tube 50 is screwed and to which the first connector 50a is connected is provided on the outer periphery of the mouthpiece 174. The other end of the mouthpiece 174 is connected to a water supply tube 31b within the universal cord 4c and the water supply tube 31b is connected to the water supply tube 31a within the operation section. The diameter "a" of the hole 181 provided in the cover member 175 is larger than the diameter "b", of the coupling section between the mouthpiece and the water supply tube 31b. Due to this, if the water supply tube 31b is damaged, the water supply tube 31b can be replaced with a new tube by disconnecting the water supply tube 31a from the water supply tube 31b within the operation section and detaching the mouthpiece 174 from the cover member 175.

Since the connector section 19 is separated from the mouthpiece 174 of the water supply tube 31b, there is no need to replace the water supply tube 31a with a new one and to disassemble the connector section 19 during the replacement of the water supply tube 31b, thereby making it possible to carry out a repair operation efficiently.

Further, compared with a case where the mouthpiece 174 is provided on the connector section 19, an operator can conveniently supply water alone using a syringe 55 without preparing a long dedicated adapter tube 50 according to this embodiment.

Figure 28:
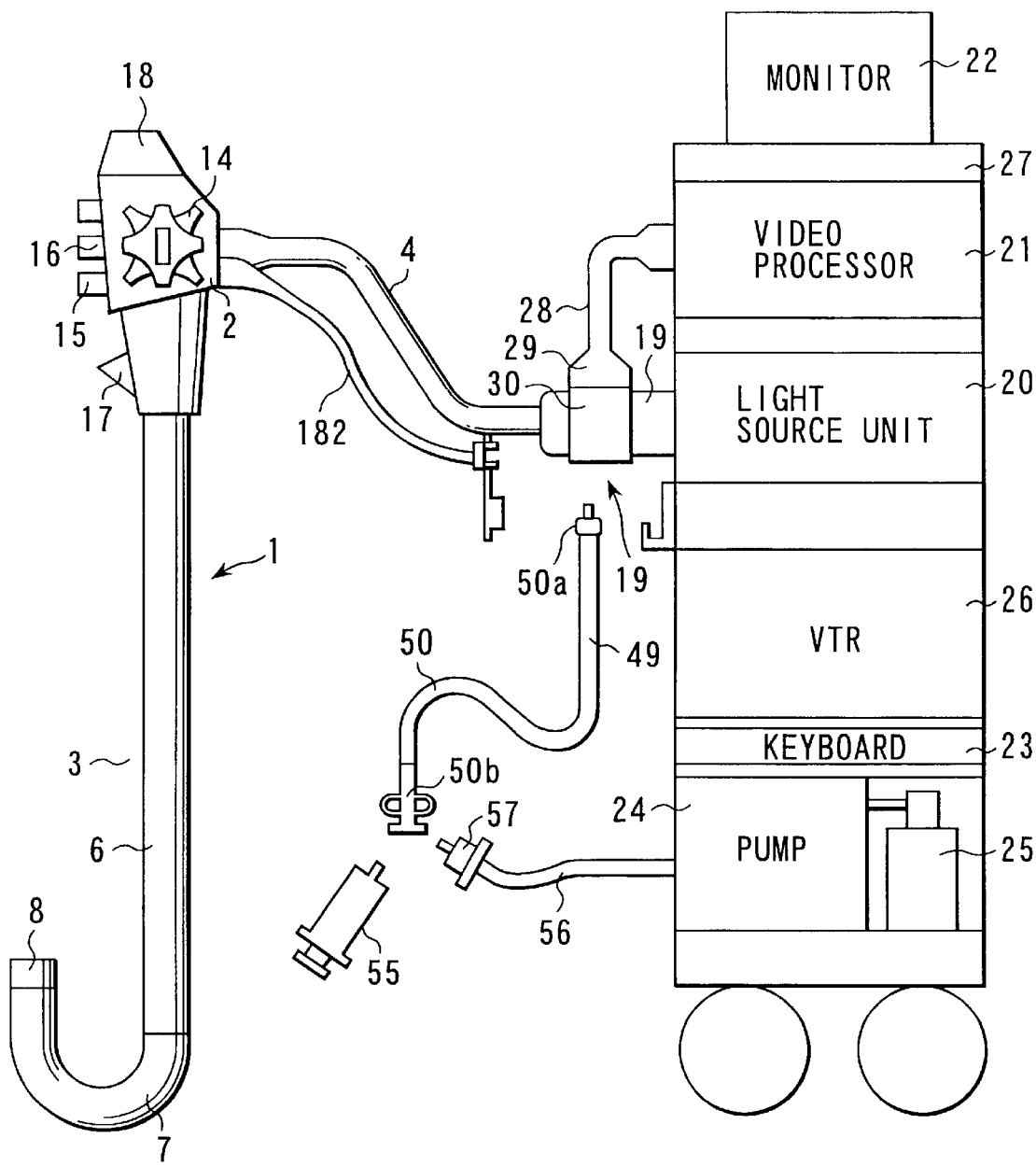
FIG. 28 is an explanatory view for schematically showing the overall constitution of an endoscope system according to the eighth embodiment of the present invention.

FIG. 28 shows an endoscope system according to the eighth embodiment of the present invention. A water supply port for connecting an adapter tube 50 is connected to an operation section independently of a universal cord 4 having an end portion. A universal cord 182 includes only a water supply tube 31b therein and the constitution of the end portion of the universal cord 182 is the same as that shown in the seventh embodiment. A water supply tube 31a is connected to the water supply tube 31b within the operation section. The universal cord 182 including the water supply tube 31b is provided separately from the universal cord 4 including the other constituent elements. If the water supply tube 31b is damaged, the water supply tube 31b can be replaced with a new tube by disconnecting the water supply tube 31b from the water supply tube 31a and detaching a mouthpiece 174 from the end portion of the universal cord 182. Since there is no need to replace the water supply tube 31a with a new one and to disassemble a connector section 19 during the replacement of the water supply tube 31b, a repair operation can be carried out efficiently. Besides, compared with a case where the mouthpiece 174 is provided on the connector section 19, an operator can conveniently supply water alone using a syringe 55 without preparing a long, dedicated adapter tube 50 according to this embodiment.

Figure 29:
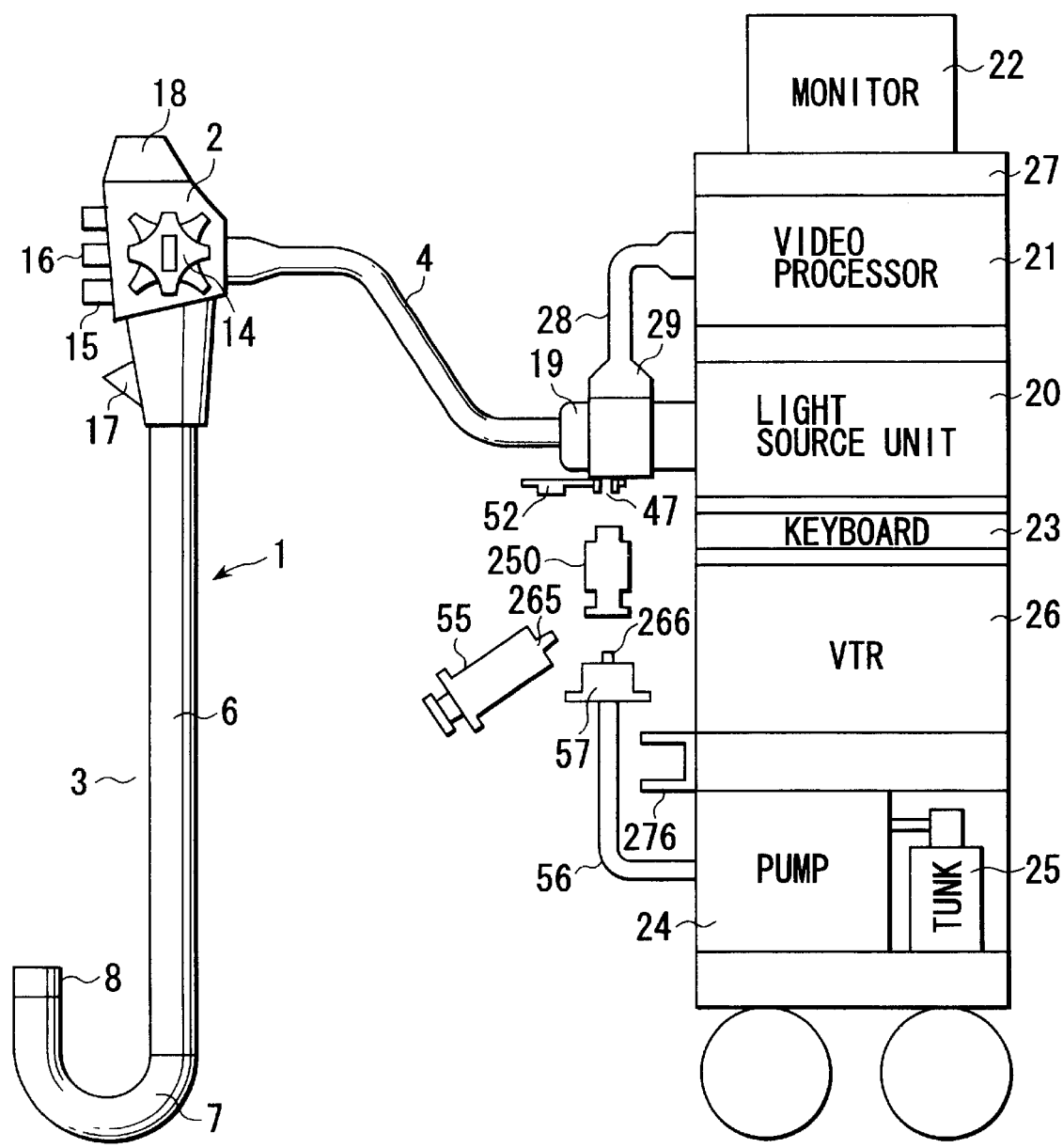
FIG. 29 is an explanatory view for schematically showing the overall constitution of an endoscope system according to the ninth embodiment of the present invention.
Figure 30:
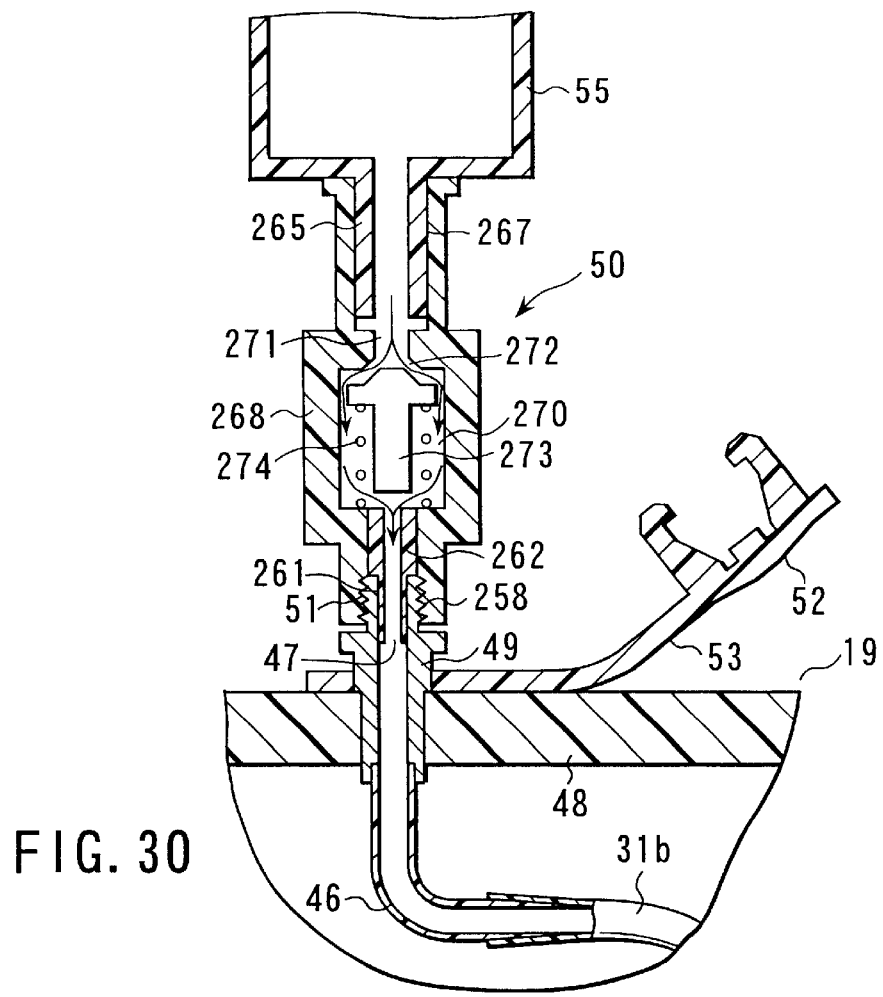
FIG. 30 is a schematic cross-sectional view showing a state in which a syringe is connected to the water supply port of the endoscope shown in FIG. 29 through an adapter.
Figure 31:
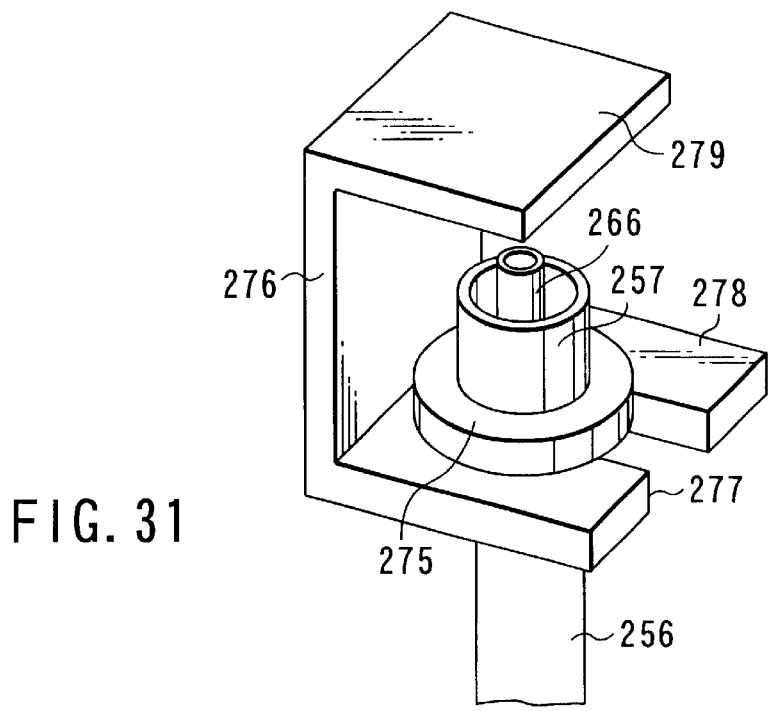
FIG. 31 is a perspective view showing a state in which the hanger member of the endoscope system shown in FIG. 29 is used.
Figure 32:
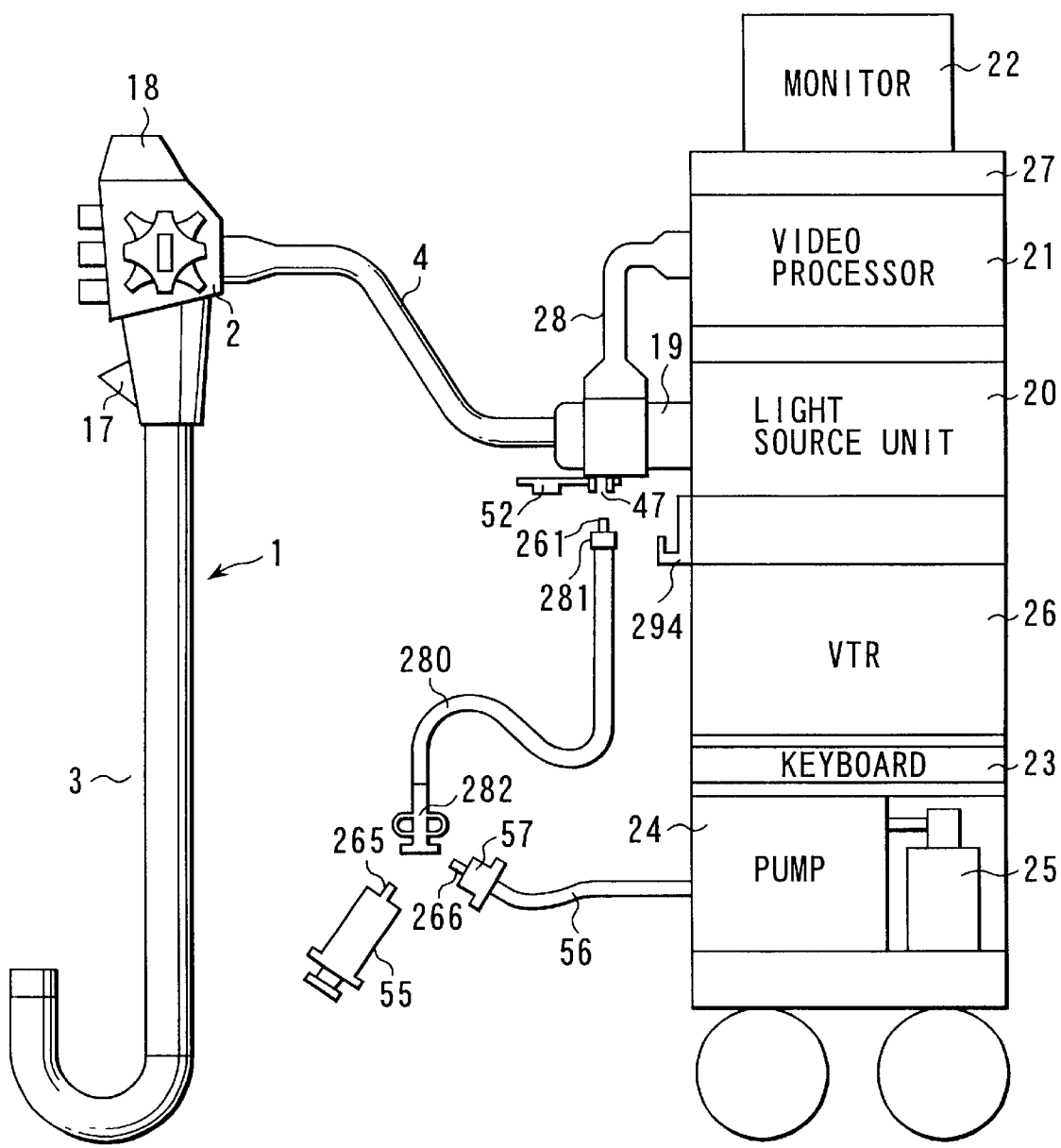
FIG. 32 is an explanatory view for schematically showing the overall constitution of an endoscope system according to the tenth embodiment of the present invention.
Figure 33:
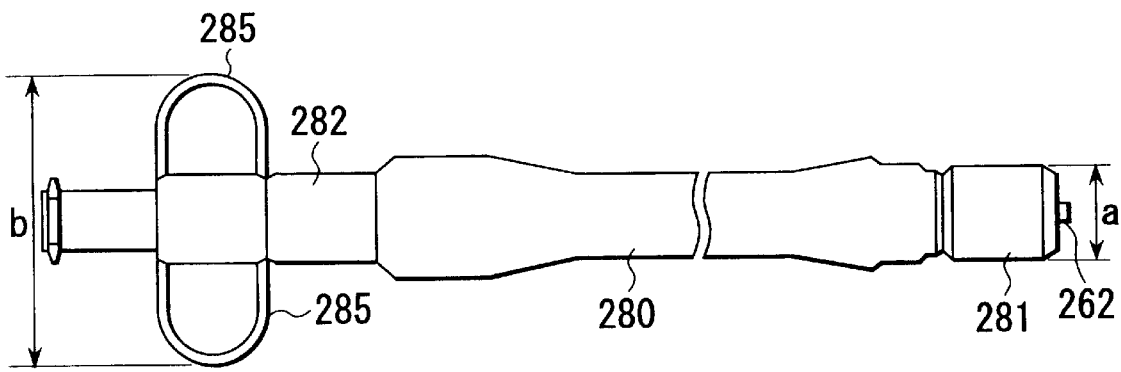
FIG. 33 is a schematic side view of the adapter tube of the endoscope system shown in FIG. 32.

FIGS. 29 to 31 schematically show an endoscope system according to the ninth embodiment of the present invention. In this embodiment, when a fluid is supplied to the forward water supply channel of an endoscope 1, the supply source of the fluid is connected to a mouthpiece 49 through an adapter 250.

In this embodiment as in the case of the above-stated first embodiment, a manually-operated water supply equipment, e.g., a syringe 55 or an automated water supply equipment, e.g., a water supply pump unit 24 can be connected as the fluid supply source. A flexible supply tube 56 is connected to the water supply pump unit 24. A connector 57 is provided on the distal end of this supply tube 56 and can be connected to the adapter 250.

As shown in FIG. 30, a female screw 258 screwed with the male screw 51 of the mouthpiece 49 is formed on one end portion of the adapter 250. A connection cylindrical portion 262 is provided on the connection section of the adapter 250 with the endoscope. The outer peripheral surface of the connection cylindrical portion 262 is formed to be tapered to conform to an inner hole 261 formed to be tapered, of the mouthpiece 49. By screwing the female screw 258 of the adapter 250 with the male screw 51 of the mouthpiece 49, the adapter 250 can be detachably connected to the mouthpiece 49. When the adapter 250 is attached to the mouthpiece 49, the inner hole 261 of the mouthpiece 49 is fixedly attached to the outer peripheral surface of the connection cylindrical portion 262.

A connection hole 267 into which the connection opening 265 of the syringe 55 or a connection opening 266 formed in the connector 57 of the supply tube 56 is fitted, is formed on the other end portion of the adapter 250. The connection hole 267 and the connection openings 265 and 266 fitted into the connection hole 267 are formed to have a taper having the same tilt angle and serve as detachable connection means. FIG. 30 shows a state in which the connection opening 265 of the syringe 55 is fitted into and connected to the connection hole 267 of the adapter 250.

Because of a Luer lock structure in which the syringe 55 or the connector 57 of the supply tube 56 is fitted into and connected to the connection hole 267 of the adapter, the syringe 55 or the connector 57 of the supply tube 56 can be sufficiently attached to or detached from the adapter 250 by rotating the adapter 250 once or less. On the other hand, if the adapter 250 is attached to or detached from the mouthpiece 49 of the endoscope 1, it is necessary to rotate the adapter 250 several times or more. Moreover, because of a structure in which the syringe 55 or the supply tube 56 is connected to the connection hole 267 on the protruding end portion of the adapter 250, an operator can attach or detach the syringe 55 or the supply tube 56 to and from the connection hole 267 of the adapter 250 more easily and naturally than the operator attaches or detaches the adapter 250 to and from the mouthpiece 49 provided in the narrow area of the endoscope 1. Normally, therefore, the syringe 55 or the supply tube 56 is connected to the connection hole 267 of the adapter 250.

A check-valve 270 for passing a fluid to be supplied only when the fluid is fed from the fluid supply source to the conduit of the endoscope 1 is incorporated into the main body member 268 of the adapter 250. The check-valve 270 has a valve hole 271 and a valve body 273 contacting with or separating from a valve seat 272 formed in the vicinity of the valve hole 271. Further, the check-valve 270 is provided with a coil spring 274 serving as an urging member urging the valve body 273 against the valve seat 272 when no fluid is fed to the forward water supply channel of the endoscope 1. The valve hole 271 and the valve seat 272 are provided to be located on the connection hole 267 side. The valve body 273 is urged by the spring 274 from the other connection cylindrical portion 262 side toward the connection hole 267 side. The valve body 273 is normally pushed against the valve seat 272 elastically to close the valve hole 271. Namely, this valve unit not only prevents backflow but also functions as a cap which is normally closed when no fluid is fed to the conduit of the endoscope 1 to shut off the leakage of the fluid from the conduit on the endoscope 1 side.

A holding flange section 275 is formed on the outer periphery of the connector 57 of the supply tube 56. The flange section 275 is provided to facilitate gripping the connector and to be used to be hooked over a hanger member 276 provided on a part of a rack 27.

As shown in FIG. 31, the hanger member 276 is formed by integrally providing a horizontal stopper piece 278 having a notch portion 277 through which the connector 57 is passed and a protruding piece 279 arranged horizontally above the horizontal stopper piece 278. By fitting the connector 57 into the notch portion 277 of the stopper piece 278 and putting and hooking the flange section 275 on the stopper piece 279, the connector 57 can be held while being stopped on the stopper piece. Further, the protruding length of the flange section 275 while holding the connector 57 is set to be slightly shorter than the distance between the stopper piece 278 and the protruding piece 279.

Due to this, the connector 57 can be fitted into the notch portion 277 only from the side toward the portion between the stopper piece 278 and the protruding piece 279. Besides, if the adapter 250 remains connected to the connector 57, the adapter 250 is struck against the protruding piece 279. Therefore, if the connector 57 is hooked over the hanger member 276, it is always necessary to detach the adapter 250 from the connector 57. As a result, an operator is forced to carry out an operation for leaving the adapter 250, detaching only the connector 57 and hooking only the connector 57 over the hanger member 276.

The hanger member 276 may be provided to be located near a light source unit 20 to which the connector 19 of the universal cord 4 is connected. By doing so, even if the supply tube 56 is long, the supply tube 56 can be hooked over the hanger member 276 without contacting the supply tube 56 with the floor. It is, therefore, possible to prevent the supply tube from being accidentally pressed with the feet and damaged.

Needless to say, the length of the supply tube 56 is set so that the supply tube 56 is not contacted with the floor when the connector 57 is connected to the adapter 250. Further, if the supply tube 56 is not hooked over the hanger member 276 but hung, the length of the supply tube 56 is set so as not to contact the distal end of the supply tube 56 with the floor.

If the above-stated endoscope 1 is used, the connector 19 of the universal cord 4 is connected to the light source unit 20. If forward water supply is not at all conducted, a cap 52 may be put on a water supply port 57 to close the port 57 as shown in FIG. 6. If it is expected to conduct forward water supply, the cap 52 is detached from the water supply port 46 and the adapter 250 is fitted into and connected to the water supply port 47. It is normally preferable that the adapter 250 is connected to the endoscope 1 before using the endoscope 1. Since the check-valve 270 is incorporated into the adapter 250 closes the valve hole 271, a fluid does not leak through the adapter 250. Accordingly, while the endoscope 1 is used, no fluid leaks outside from the inlet of the forward water supply channel of the endoscope 1 even if the syringe 55 or the supply tube 56 is not connected to the adapter 250.

If forward water supply is commenced, the syringe 55 or the connector 57 of the supply tube 56 is selected and connected to the connection hole 267 of the adapter 250. Then, the roller pump, for example, of the forward water supply pump unit 24 is driven and water supply is selectively carried out by operating the syringe if the syringe 55 is connected or by operating the switch if the supply tube 56 is connected. At this moment, the check-valve 270 is opened by the pressure of supplied water and water is supplied to the forward water supply channel of the endoscope 1.

When the use of the endoscope 1 is finished, the syringe 55 or the supply tube 56 is detached from the adapter 250 while keeping the adapter 250 connected to the endoscope 1 and the endoscope 1 is carried from a checking room to a clean room.

As stated above, the adapter 250 functions as a cap covering the water supply port 47. Therefore, it is possible to prevent water remaining in the forward water supply channel from leaking outside from the water supply port 47, and prevent the external device, such as the VTR 26 from being damaged by the water dosing on it.

Here, since the adapter 250 is connected to the mouthpiece 49 of the endoscope 1 with a screw, it is required to rotate the adapter 250 several times or more to attach or detach the adapter 250. On the other hand, the connection of the syringe 55 or the connector 57 of the supply tube 56 to the adapter 250 is based on the Luer lock structure which facilitates attachment/detachment operations. Therefore, an operator rather selects attaching and detaching the syringe 55 or the connector 57 of the supply tube 56 to and from the connection hole 267 of the adapter 250 protruding from the connector 19 of the universal cord 4 while keeping the adapter 250 connected to the mouthpiece 49 provided in the narrow area of the endoscope 1. Namely, since the adapter 250 is kept connected to the water supply port 47, the water remaining in the forward water supply channel does not leak outside from the water supply port 47 and the endoscope 1 can be handled hygienically.

If the endoscope 1 is washed and sterilized while attaching the adapter 250 to the endoscope 1, a cleaning solvent or sterilizing agent can be fed from the adapter 250 into the forward water supply channel of the endoscope 1.

Since the adapter 250 having the above-stated valve unit is employed, it is not necessary to provide a check-valve on the main body of the endoscope 1. It is, therefore, possible to simplify the structure of the endoscope 1, to make the endoscope 1 lighter in weight and smaller in size and to reduce the production cost of the endoscope 1. Besides, since no complex check-valve is provided on the endoscope 1, no defect relating to the check-valve occurs. Thus, no repair operation for the defect of the endoscope is conducted.

Moreover, since the endoscope 1 can be made small in size and light in weight, the operativity of the endoscope 1 is improved and the endoscope 1 can be easily carried.

FIGS. 32 to 35 show the tenth embodiment of the present invention.

According to the tenth embodiment, an adapter tube 280 having a check-valve instead of the above-stated adapter 250 is used as an endoscope valve unit. The first connector section 281 constituting an endoscope connection section connected to the water supply port 47 of an endoscope 1 is provided on the distal end of the tube 280. The second connector section 282 constituting a mouthpiece serving as a connection section connected to a syringe 55 or the connector 57 of a supply tube 56 is provided on the proximal end portion of the tube 280.

The first connector section 281 has a female screw (which is the same as the female screw denoted by reference symbol 258 in FIG. 30) screwed with the male screw 51 of a mouthpiece 49 and has a connection cylindrical section 262 formed to be tapered so as to be fitted into the inner hole 261 of the mouthpiece 49 as in the case of the ninth embodiment.

The second connector section 262 is, as in the case of the first embodiment, has a Luer lock structure, i.e., has a Luer taper connection hole section 267 formed therein, which can be fitted into and connected to either the connection opening 265 of a syringe 55 or a connection hole 266 formed in the connector 57 of a supply tube 56.

The second connector section 282 is constituted as a grip section which can be gripped more easily than the first connector section 281. Here, a pair of grip ring sections 285 horizontally protruding are provided on the outer wall surface of the main body of the second connector section 282. The width of the second connector section including the paired grip ring sections 285 is "b", which is larger than the outside diameter "a" of the first connector section 281. Besides, the second connector section 282 can be arranged in a free space away from the narrow area of the connector 19 of the endoscope 1 through the long flexible tube 280.

Further, while the first connector section 281 is kept fitted into and connected to the water supply port 47 of the endoscope 1, the syringe 55 or the connector 57 of the supply tube 56 can be easily connected to the second connector section 282 by the Luer lock structure. While the inlet of a conduit formed in the endoscope 1 is connected to the first connector section 281 by screw connection which requires laborious attachment/detachment operations while the second connector is connected to a fluid supply source by plug-in type connection which can only require simple attachment/detachment operations.

In the connection between the inlet of the conduit formed in the endoscope 1 and the first connection section 281, if the attachment/detachment operations are laborious, the connection method is not necessarily a screw connection method but may be a plug-in type connection method. Further, if the attachment/detachment operations for attaching and detaching the second connector section 282 to and from the fluid supply source can be easily conducted, the connection method is not necessarily a plug-in type connection method but may be a screwing connection method. In either case, various connection methods including conventional methods and well-known methods can be selected. In any case, the attachment/detachment of the connection section between the inlet of the conduit formed in the endoscope 1 and the first connector section 281 is constituted to be more complicated than that of the connection section between the second connector section 282 and the fluid supply source.

Figure 34:
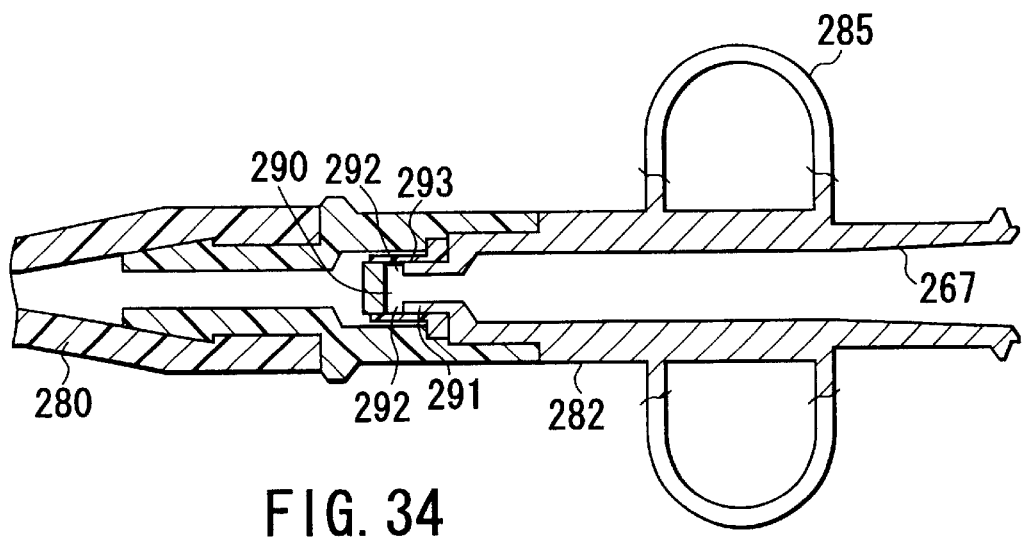
FIG. 34 is a longitudinal sectional view of the second connector section of the check-value equipped adapter tube of the endoscope system shown in FIG. 32.

As shown in FIG. 34, a check-valve 290 for passing a fluid to be supplied only when the fluid is fed from the fluid supply source to the conduit of the endoscope 1 is incorporated into the second connector section 282. The check-valve 290 has a cylindrical valve seat member 291 having a distal end sealed and a plurality of valve holes 292 are formed on the peripheral wall of the valve seat member 291. A tubular elastic film 293 is closely attached to and covers the outer periphery of the valve seat member 291. The tubular elastic film 293 is normally closely attached to the outer periphery of the valve seat member 291 to thereby block the plurality of valve holes 292 and shut off a supply channel. When a fluid is fed from the second connector section 292, the elastic film 293 is lifted from the outer peripheral surface of the valve seat member 291 by fluid pressure acting on the valve holes 292 to thereby open the valve holes 292. As a result, the fluid can flow in the endoscope 1. Further, if there is a backflow fluid, the elastic film 293 is pushed against and closely attached to the outer periphery of the valve seat member 291, with the result that the valve holes 292 are closed and the backflow of the fluid is shut off.

Figure 35:
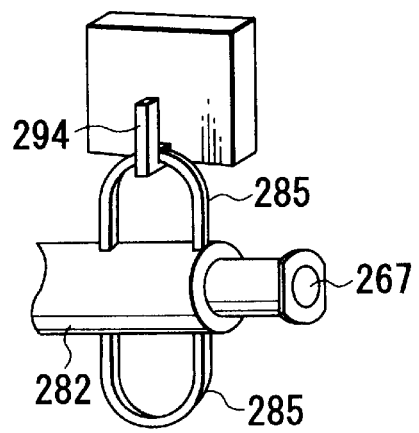
FIG. 35 is a perspective view showing a state in which the grip ring section of the adapter tube is hooked over a hook section.

The grip ring section 285 provided on the second connector section 282 is designed to be able to be hooked over a hook section 294 formed on a part of a rack 27 on which peripheral equipment are disposed (see FIG. 35).

Here, the length of the tube 280 is about 1000 mm. If the light source unit 20 is located to facilitate attaching/detaching the connector 19, i.e., 1000 mm or higher above the floor, it is possible to prevent the second connector section 29 from being contacted with the floor even while the second connector section 292 is hung without being hooked over the hook section 294.

According to a preferred embodiment, the inside diameter of the conduit of the forward water supply channel of the endoscope 1 is about 1.5 mm and the inside diameter of the conduit of the tube 280 is about 3 mm. If a conduit is thin, the resistance of the conduit increases and power for operating a syringe increases. However, since the conduit of the tube 280 has a large inside diameter, power for operating the syringe 55 is lower and the syringe 55 can be operated easily.

Further, if the length of the conduit of the forward water supply channel of the endoscope 1 is about 3500 mm and the length of the conduit of the tube 280 is about 1000 mm, the capacity of the conduits is about 6.19+7.07=13.26 cc in all. Accordingly, if the syringe 55 having a capacity of 30 cc is used, water can be surely supplied to the endoscope 1 with only one operation. The tube 280 stated above is designed that way.

According to this embodiment, the syringe 55 or the connector 57 of the supply tube 56 is connected to the water supply port 47 of the endoscope 1 through the adapter tube 280 having the check-valve. Due to this, load exerted on the connector 19 of the universal cord 4 can be reduced. If the syringe 55 or the connector 57 of the supply tube 56 is directly connected to the connector 19 of the universal cord 4 of the endoscope 1, an attachment or detachment force is directly applied to the connector 19 connected to the light source unit 20 and an excessive force is applied to the connection portion of the connector 19 with the light source unit 31 to thereby possibly cause a defect such as a contact fault. However, since the syringe 55 or the supply tube 56 is connected to the water supply port 47 of the connector 19 of the endoscope 1 through the adapter tube 280, a force is not transferred to the connection portion with the light source unit, thereby preventing such defects.

Since various mouthpieces, contacts and the like, not shown, are provided as well as the water supply port 47 in the vicinity of the connector 19 of the endoscope 1, there is not enough space. However, since the valve unit is not incorporated into the first connector section 281 but into the second connector section 282, the first connector section 281 can be made simple and small. Thus, it is possible to constitute a connection section provided in the vicinity of the connector 19 which has little space, in a compact fashion.

The adapter tube 280 is constituted such that the second connector 282 is a grip section easier to grip than the first connector 281. The second connector section 282, to which the syringe 55 or the supply tube 56 is connected, can be arranged in a free space away from the narrow area of the connector 19 of the endoscope 1 through the long tube 280. This can facilitate connecting the syringe 55 or the supply tube 56 to the second connector 282. That is to say, while the adapter tube 280 is connected to the connector 19 of the endoscope 1, the syringe 55 or the supply tube 56 can be connected to the second connector section 282 of the adapter tube 280, thereby making it possible to facilitate the attachment/detachment operations and to improve the operativity of the endoscope 1. Further, since the adapter tube 280 is somewhat long, a person responsible for a checking operation can conduct a water supply operation by oneself when supplying water using the syringe 55. Besides, it is possible to easily conduct the water supply operation at a position which does not hamper the operation of an assistant such as a nurse.

The eleventh embodiment of the present invention will be described with reference to FIGS. 36 to 38.

In this embodiment, a water supply port 300 communicating with a forward water supply channel is provided on the operation section of an endoscope 1. The same adapter tube 280 having a check-valve as that in the tenth embodiment is also prepared. The connector section 281 of the tube 280 can be connected to the water supply port 300.

A fingertip clip 301 is employed to bind the adapter tube 280 with the universal cord 4 of the endoscope 1. The binding clip 301 has the first holding section 302 into which the adapter tube 280 is fitted and by which the adapter tube 280 is elastically held and the second holding section 303 into which the universal cord 4 is fitted and by which the universal cord 4 is elastically held, as shown in FIGS. 37 and 38. The first holding section 302 and the second holding section 303 are coupled to each other back to back.

If the adapter tube 280 is bound with the universal cord 4 of the endoscope 1 using the binding clip 301 as described above, the adapter tube 280 does not sway to and fro and does not become an obstruction while conducting checking operations or carrying the endoscope 1 from a checking room to a cleaning room, thereby improving the operativity of the endoscope 1.

The present invention should not be limited to the above-stated embodiments and can be applied to, for example, a case of connecting the endoscope to the inlet of a water supply conduit (including an auxiliary water supply conduit) communicating with a water supply nozzle toward the observation window or a case of employing a treatment tool channel as a water supply conduit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an insertion section having a proximal end portion and a distal end portion, and being insertable into a body cavity;
    an operation section arranged on a proximal end portion side of the insertion section;
    a universal cord extending from the operation section, and having a distal end portion; and
    a conduit inserted into said insertion section, said operation section and said universal cord, wherein the conduit has one end arranged on the distal end portion of said insertion section and having a first opening portion formed therein, and the other end arranged on said universal cord and having a second opening portion formed therein, the conduit comprising a plurality of tubes, which are separably connected by a connecting member, the connecting member being provided inside the endoscope.

2. An endoscope according to claim 1, wherein said conduit has a separable portion arranged in the operation section.

3. An endoscope according to claim 1, wherein said conduit includes a conduit selected from a group consisting of a forward water supply conduit, an air/water supply conduit, a suction conduit and an air supply conduit.

4. An endoscope according to claim 2, wherein said conduit includes a conduit selected from a group consisting of a forward water supply conduit, an air/water supply conduit, a suction conduit and an air supply conduit.

5. An endoscope according to claim 1, wherein said conduit has a first flexible tube extended in said insertion section, a second flexible tube extended in the universal cord and a connection member connecting the first and second flexible tubes in a dividable manner, the connection member having a channel communicating with the first and second flexible tube.

6. An endoscope according to claim 2, wherein said conduit has a first flexible tube extended in said insertion section, a second flexible tube extended in the universal cord and a connection member connecting the first and second flexible tubes in a dividable manner, the connection member having a channel communicating with the first and second flexible tube.

7. An endoscope according to claim 5, wherein said second flexible tube has a curved portion which is arranged in the operation section and around which a coil is wound.

8. An endoscope according to claim 6, wherein said second flexible tube has a curved portion which is arranged in the operation section and around which a coil is wound.

9. An endoscope according to claim 5, wherein said connection member has a curved rigid pipe.

10. An endoscope according to claim 6, wherein said connection member has a curved rigid pipe.

11. An endoscope comprising:
an insertion section having a proximal end portion and distal end portion, and being insertable into a body cavity;
an operation section arranged on a distal end portion side of the insertion section;
a universal cord extending from the insertion section, and having a distal end portion;
a connector provided on the distal end portion of the universal cord; and
a conduit extended in said insertion section, said operation section and said universal cord, wherein
the conduit has one end arranged on the distal end portion of said insertion section and having a first opening portion formed therein, and the other end arranged on said connector and having a second opening portion formed therein, the conduit comprising a plurality of tubes, which are separably connected by a connecting member, the connecting member being provided inside the endoscope.

12. An endoscope according to claim 11, wherein said conduit has a separable portion arranged in the operation section.

13. An endoscope according to claim 11, wherein said conduit includes a conduit selected from a group consisting of a forward water supply conduit, an air/water supply conduit, a suction conduit and an air supply conduit.

14. An endoscope according to claim 12, wherein said conduit includes a conduit selected from a group consisting of a forward water supply conduit, an air/water supply conduit, a suction conduit and an air supply conduit.

15. An endoscope according to claim 11, wherein said conduit has a first flexible tube extended in said insertion section, a second flexible tube extended in the universal cord and a connection member connecting the first and second flexible tubes in a separable manner, the connection member having a channel communicating with the first and second flexible tube.

16. An endoscope according to claim 12, wherein said conduit has a first flexible tube extended in said insertion section, a second flexible tube extended in the universal cord and a connection member connecting the first and second flexible tubes in a separable manner, the connection member having a channel communicating with the first and second flexible tube.

17. An endoscope according to claim 15, wherein said second flexible tube has a curved portion which is arranged in the operation section and around which a coil is wound.

18. An endoscope according to claim 16, wherein said second flexible tube has a curved portion which is arranged in the operation section and around which a coil is wound.

19. An endoscope according to claim 15, wherein said connection member has a curved rigid pipe.

20. An endoscope according to claim 16, wherein said connection member has a curved rigid pipe.

21. An endoscope system comprising:
an insertion section having a proximal end portion and a distal end portion, and inserted into a body cavity;
an operation section arranged on a proximal end portion side of the insertion section;
a universal cord extending from the operation section, and having a distal end portion;
a connector provided on the distal end portion of the universal cord;
a conduit extended in said insertion section, said operation section and said universal cord, and having one end arranged on the distal end portion of said insertion section and having a first opening portion formed therein and the other end arranged on said connector and having a second opening portion formed therein;
a fluid supply source supplying a fluid to said conduit;
an adapter having a first connection section attachable and detachable to said second opening portion and a second connection section attachable and detachable to said fluid supply source; and
a valve which is provided in the adapter and prevents backflow of the fluid.

22. An endoscope system according to claim 21, wherein said valve is capable of communicating the fluid in a direction from said connection section to said first connection section.

23. An endoscope system according to claim 21, wherein said first connection section and said second connection section are screwed to each other, and said fluid supply source and said second connection section are plug-in connected to each other.

24. An endoscope system according to claim 23, wherein said fluid supply source and said second connection section are connected by engaging a Luer taper connection hole formed in said second connection section with said fluid supply source.

25. An endoscope system according to claim 21, wherein said valve is provided on said second connection section.

26. An endoscope system according to claim 21, wherein said adapter has one of a hook and a ring provided near the second connection section.

27. An endoscope system according to claim 21, further comprising a clip for fixing said adapter to the universal cord.

28. An endoscope system according to claim 21, wherein said valve has a valve seat, a valve body capable of being lifted from the valve seat, and an urging member pressing the valve body against the valve seat and closing the valve when no fluid is supplied to said conduit.

29. An endoscope system according to claim 21, wherein said valve has a valve seat, a valve body capable of being lifted from the valve seat, and an urging member pressing the valve body against the valve seat and closing the valve when no fluid is supplied to said conduit.

30. An endoscope system according to claim 28, wherein said urging member has a spring.

31. An endoscope system according to claim 29, wherein said urging member has a spring.

32. An endoscope system according to claim 21, wherein said valve has an elastic film covering and closing a valve hole, the elastic film capable of opening the valve hole by fluid pressure acting on the valve hole when the fluid is fed to said conduit.

33. An endoscope system according to claim 21, wherein said valve has an elastic film covering and closing a valve hole, the elastic film capable of opening the valve hole by fluid pressure acting on the valve hole when the fluid is fed to said conduit.

34. An endoscope system according to claim 32, wherein said elastic film is made of rubber.

35. An endoscope system according to claim 33, wherein said elastic film is made of rubber.

* * * * *